United States Patent
Kato et al.

(10) Patent No.: US 6,294,555 B1
(45) Date of Patent: Sep. 25, 2001

(54) 1-[(1-SUBSTITUTED-4-PIPERIDINYL) METHYL]-4-PIPERIDINE DERIVATIVE, PROCESS FOR PRODUCING THE SAME, MEDICINAL COMPOSITIONS CONTAINING THE SAME AND INTERMEDIATES OF THESE COMPOUNDS

(75) Inventors: Shiro Kato, Sakai; Yoshihito Toyotomi, Kawanishi; Hirotake Tateishi, Neyagawa; Hiroshi Harada, Suita; Naoyuki Yoshida, Sakai; Kazuo Morikage; Yukiko Morikage, both of Suita, all of (JP)

(73) Assignee: Dainippon Pharmaceutical Co., Ltd., Osaka-Fu (JP)

( * ) Notice: Subject to any disclaimer, the term of this patent is extended or adjusted under 35 U.S.C. 154(b) by 0 days.

(21) Appl. No.: 09/674,162

(22) PCT Filed: Apr. 19, 1999

(86) PCT No.: PCT/JP99/02056

§ 371 Date: Oct. 27, 2000

§ 102(e) Date: Oct. 27, 2000

(87) PCT Pub. No.: WO99/55674

PCT Pub. Date: Nov. 4, 1999

(30) Foreign Application Priority Data

Apr. 28, 1998 (JP) .................................................. 10-134504
Jun. 24, 1998 (JP) .................................................. 10-195019

(51) Int. Cl.[7] ..................... A61K 31/445; C07D 401/06; C07D 405/14

(52) U.S. Cl. ......................... 514/316; 546/187; 546/188; 546/189; 546/190

(58) Field of Search ............................. 514/316; 546/187, 546/188, 189, 190

(56) References Cited

U.S. PATENT DOCUMENTS 5,864,039 1/1999 Kawakita et al. .

FOREIGN PATENT DOCUMENTS

| 0445862 | 9/1991 | (EP) . |
| 7-504428 | 5/1995 | (JP) . |
| 11-001472 | 1/1999 | (JP) . |
| 11-1472 | 1/1999 | (JP) . |
| 93/18027 | 9/1993 | (WO) . |

OTHER PUBLICATIONS

Merck Index, 12 ed., entry 2377 (1996).
Craig et al., "Pharmacological Characterization of a Neuronal Receptor for 5–Hydroxytryptamine in Guinea Pig Ileum with Properties Similar to the 5–Hydroxytryptamine$_4$ Receptor[1]", J. Pharmacol. Exp. Ther., 1990, 252, 1378–1386.

Yoshida et al., "AS–4370, a New Gastrokinetic Agent, Enhances Upper Gastrointestinal Motor Activity in Consciuos Dogs", J. Pharmacol. Exp. Ther., 1991, 257, 781–787.

Primary Examiner—C. S. Aulakh
(74) Attorney, Agent, or Firm—Wenderoth, Lind & Ponack, L.L.P.

(57) ABSTRACT

Compound of the formula (I):

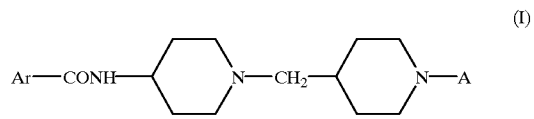

wherein Ar is a group of the following formula (Ar-1) or (Ar-2):

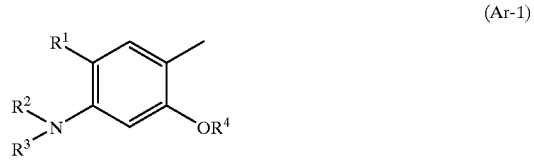

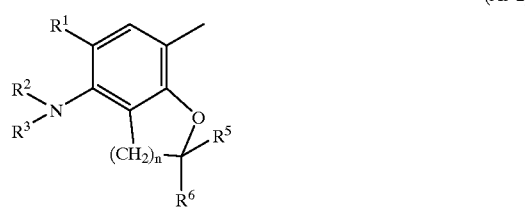

A is a group of the formula:

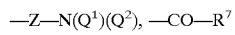

or

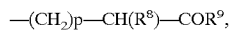

or a pharmaceutically acceptable acid addition salt thereof, a process for preparing the same, a pharmaceutical composition containing the same, and intermediates therefor. The compounds of the present invention show a potent affinity for 5-HT$_4$ receptors, and they are useful as a gastrointestinal motility enhancer or a gastrointestinal prokinetic agent.

19 Claims, No Drawings

1-[(1-SUBSTITUTED-4-PIPERIDINYL) METHYL]-4-PIPERIDINE DERIVATIVE, PROCESS FOR PRODUCING THE SAME, MEDICINAL COMPOSITIONS CONTAINING THE SAME AND INTERMEDIATES OF THESE COMPOUNDS

TECHNICAL FIELD

The present invention relates to a novel 1-[(1-substituted-4-piperidinyl)methyl]-4-piperidine derivative exhibiting a potent agonistic activity on serotonin 4 receptors (hereinafter, occasionally referred to as 5-HT$_4$ receptors).

More particularly, the present invention relates to a 1-[(1-substituted-4-piperidinyl)methyl]-4-piperidine derivative forming an amide with a 4-amino-5-halogenobenzoic acid or a 4-amino-5-halogeno-2,3-dihydrobenzo[b]furan-7-carboxylic acid, a process for the preparation thereof, a pharmaceutical composition containing the same, and an intermediate therefor.

BACKGROUND ART

WO-95-26953 Publication discloses that the compounds of the following formula (P-1), etc. have selective antagonistic effects on 5-HT$_4$ receptors, and are useful for the prophylaxis or treatment of various gastrointestinal diseases, etc.

(P-1)

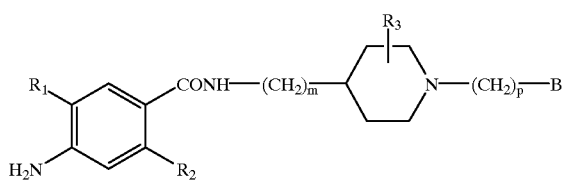

wherein R$_1$ is a halogen atom, R$_2$ is a lower alkoxy group, etc., m is 1 or 2, p is an integer of 1 to 6, B is a group of the formula:

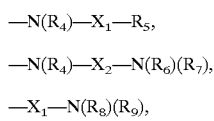

or

(X$_1$ is CO, CS or SO$_2$, X$_2$ is CO or CS, R$_4$ is a hydrogen atom, a lower alkyl group, etc., R$_6$ and R$_7$ are a lower alkyl group, etc., or R$_6$ and R$_7$ may combine together with the adjacent nitrogen atom to form a ring, R$_8$ and R$_9$ are a lower alkyl group, etc., or R$_8$ and R$_9$ may combine together with the adjacent nitrogen atom to form a ring, Het is a 5- or 6-membered, mono- or bicyclic heterocycle group having an amide or urea in the ring and having 1–5 heteroatom(s) selected from oxygen atom, sulfur atom and nitrogen atom, and the definitions for some substituents are omitted)

The compounds of the present invention of the formula (I) as mentioned below are distinguished from the compounds of the formula (P-1) having an amide-bond and a piperidine moiety bonded each other via an alkylene, and further having different substituents at the 1-position of the piperidine ring.

In addition, EP-A-445862 (=JP-A-04-211685) Publication discloses that N-(4-piperidinyl)(dihydrobenzofuran or dihydro-2H-benzopyran)carboxamide derivatives of the following formula (P-2) exhibit gastrointestinal motility stimulation properties.

(P-2)

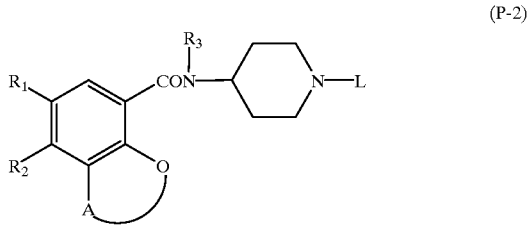

wherein A is a group of the following formula:

 (a-1);

 (a-2);

or

 (a-3);

R$_1$ is a hydrogen atom or a halogen atom, R$_2$ is a hydrogen atom, an amino group, etc., R$_3$ is a hydrogen atom, a C$_{1-6}$ alkyl group, etc., L is a C$_{3-6}$ cycloalkyl group, etc., L is a group of the formula:

 (b-1);

 (b-2);

 (b-3);

or

 (b-4);

(each Alk is a C$_{1-6}$ alkanediyl group, R$_4$ is a hydrogen atom, a cyano group, a C$_{1-6}$ alkysulfonylamino group, a C$_{3-6}$ cycloalkyl group, a C$_{5-6}$ cycloalkanone group, an aryl group, a di(aryl)-methyl group, or Het (Het is a 5- or 6-membered heterocyclic group having 1, 2, 3 or 4 heteroatom(s) selected from oxygen, sulfur and nitrogen, etc.), R$_5$ is a hydrogen atom, a C$_{1-6}$ alkyl group, etc., X is O, S, SO$_2$ or NR$_6$ (R$_6$ is a hydrogen atom, a C$_{1-6}$ alkyl group or an aryl group), R$_7$ is a hydrogen atom, a C$_{1-6}$ alkyl group, etc., Y is NR$_8$ or a direct bond (R$_8$ is a hydrogen atom, a C$_{1-6}$ alkyl group or an aryl group), R$_9$ and R$_{10}$ are independently a hydrogen atom, a C$_{1-6}$ alkyl group, etc., or R$_9$ and R$_{10}$ may combine together with the nitrogen atom to which R$_9$ and R$_{10}$ bond to form a pyrrolidinyl or piperidinyl ring being optionally substituted with a C$_{1-6}$ alkyl group, an amino group, etc., or R$_9$ and R$_{10}$ may combine together with the nitrogen atom to which R$_9$ and R$_{10}$ bond to form a piperazinyl or 4-morpholinyl ring being optionally substituted with a C$_{1-6}$ alkyl group, and the definitions for some substituents are omitted).

Among the compounds of the above formula (P-2), when R$_4$ is Het and said Het is a piperidine, the compound of the formula (P-2) may theoretically be overlapped with some of the compounds of the formula (I) of the present invention, but said EP Publication exemplifies as such compounds only a compound of the formula (P-2') (Compound 57):

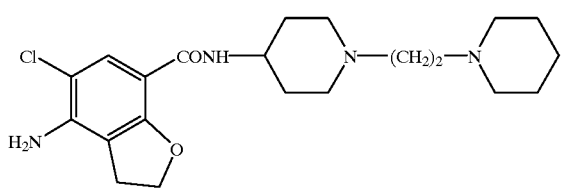

The compound of the above formula (P-2') has an unsubstituted piperidine bonded at the 1-position thereof, which is quite different from the compounds (I) of the present invention, because the present compound (I) has a piperidine ring having a specific substituent (i.e., A) at the 1-position of said piperidine ring, and said piperidine ring is bonded at the 4-position thereof, as described below.

At the present, cis-4-amino-5-chloro-N-[1-[3-(4-fluorophenoxy)-propyl]-3-methoxy-4-piperidinyl]-2-methoxybenzamide (general name; cisapride, cf., Merck Index, 12 ed., 2377 (1996)) has widely been used in the clinical field as a gastrointestinal motility enhancer or as a gastrointestinal prokinetic agent. Recently, 5-HT$_4$ receptors were found during the studies on serotonin receptors being participated in gastrointestinal motility stimulation by metoclopramide or cisapride, and it has been confirmed that these benzamide derivatives enhance the gastrointestinal motility by stimulating 5-HT$_4$ receptors (cf., J. Pharmacol. Exp. Ther., 1990, 252, 1378; J. Pharmacol. Exp. Ther., 1991, 257, 781). Thus, a compound stimulating 5-HT$_4$ receptors being widely distributed throughout the gastrointestinal organs may be expected to enhance the gastrointestinal motility, but cisapride as mentioned above shows disadvantageously inhibitory effects on the central nervous system based on the antagonistic activity against dopamine D$_2$ receptors, or side effects on the heart. Therefore, it is difficult to use cisapride in the clinical field. Besides, there is a growing tendency to increase patients being suffering from symptoms associated with gastrointestinal motor disorders due to the complicated society and aging society, and under these circumstances, it has been strongly desired to develop an excellent gastrointestinal prokinetic agent.

DISCLOSURE OF INVENTION

The present inventors have intensively studied on 1-[(1-substituted-4-piperidinyl)methyl]-4-piperidine derivative acting on 5-HT$_4$ receptors, and have found that a 1-[(1-substituted-4-piperidinyl)-methyl]-4-piperidine derivative forming an amide with a 4-amino-5-halogenobenzoic acid or a 4-amino-5-halogeno-2,3-dihydrobenzo[b]-furan-7-carboxylic acid shows a potent agonistic activity on 5-HT$_4$ receptors, and is useful as an excellent gastrointestinal motility enhancer or as an excellent gastrointestinal prokinetic agent, and finally have accomplished the present invention.

An object of the present invention is to provide a novel 1-[(1-substituted-4-piperidinyl)methyl]-4-piperidine derivative having a potent agonistic activity on 5-HT$_4$ receptors, more particularly, to provide a 1-[(1-substituted-4-piperidinyl)methyl]-4-piperidine derivative forming an amide with a 4-amino-5-halogenobenzoic acid or a 4-amino-5-halogeno-2,3-dihydrobenzo[b]furan-7-carboxylic acid. Especially, the present invention provides a compound being useful as a gastro-intestinal motility enhancer or as a gastrointestinal prokinetic agent. Another object of the present invention is to provide a process for preparing said compound. Still further object of the present invention is to provide a pharmaceutical composition containing said compound. Further object of the present invention is to provide an intermediate for preparing said compound. These and other objects and advantages of the present invention are obvious to any person skilled in the art from the following disclosure.

The present invention provides a 1-[(1-substituted-4-piperidinyl)methyl]-4-piperidine derivative of the following formula (I), a pharmaceutically acceptable acid addition salt thereof, a process for preparing the same, and a pharmaceutical composition containing the same:

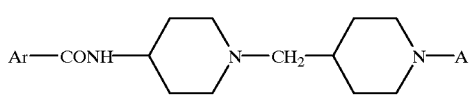

wherein Ar is a group of the following formula (Ar-1) or (Ar-2):

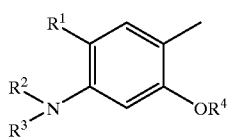

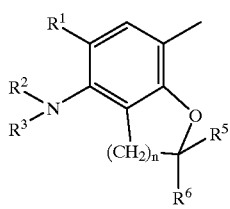

(in which R$^1$ is a halogen atom,
R$^2$ is a hydrogen atom or a lower alkyl group,
R$^3$ is a hydrogen atom, a lower alkyl group, or a lower alkanoyl group,
R$^4$ is a hydrogen atom or a lower alkyl group,
R$^5$ and R$^6$ are the same or different and each a hydrogen atom or a lower alkyl group, and
n is 1,2 or 3),
A is a group of the following formula (A-1), (A-2) or (A-3):

$$—Z—N(Q^1)(Q^2) \qquad (A-1)$$

(in which Z is —CO—, —CS— or —SO$_2$—,
Q$^1$ and Q$^2$ are the same or different and each a hydrogen atom, a lower alkyl group, a cycloalkyl group, a substituted or unsubstituted phenyl group, or a substituted or unsubstituted phenyl-lower alkyl group, or Q$^1$ and Q$^2$ may combine together with the nitrogen atom to which they bond to form a pyrrolidine ring, a piperidine ring, a hexahydroazepine ring, a morpholine ring, a thiomorpholine ring, or a piperazine ring having optionally a lower alkyl or benzyl substituent on the other nitrogen atom);

$$—CO—R^7 \qquad (A-2)$$

(in which R$^7$ is a hydrogen atom, a lower alkyl group, a lower alkoxy group, a lower alkoxycarbonyl group, a lower alkyl group being substituted by a hydroxy, lower alkoxy or lower alkoxycarbonyl group, or a substituted or unsubstituted phenyl group);

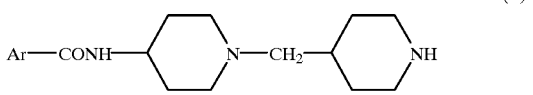

(A-3)

(in which p is 0, 1, 2, 3, 4 or 5,
R$^8$ is a hydrogen atom or a lower alkyl group, and
R$^9$ is a lower alkyl group or a lower alkoxy group), and also provides an intermediate of the following formula (II) (hereinafter, occasionally simply referred to as the intermediate (II)) or an acid addition salt thereof:

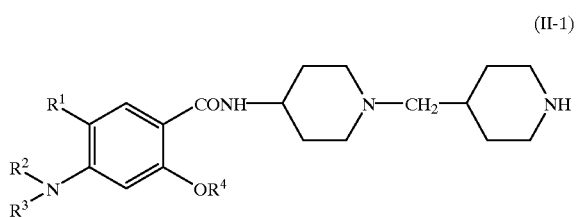

(II)

wherein Ar is the same as defined above, that is, when Ar is a group of the above formula (Ar-1), an intermediate of the formula (II-1):

(II-1)

or when Ar is a group of the above formula (Ar-2), an intermediate of the formula (II-2):

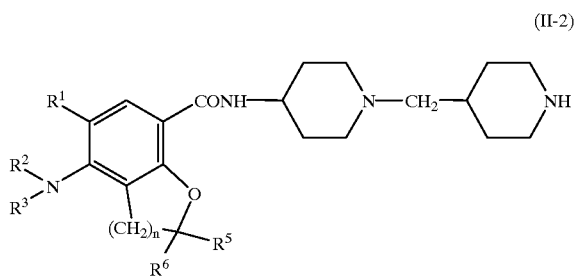

(II-2)

and further provides an intermediate of the following formula (VIII) (hereinafter, occasionally simply referred to as the intermediate (VIII)) or an acid addition salt thereof:

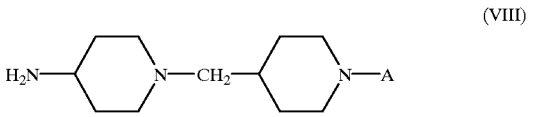

(VIII)

wherein A is the same as defined above.

The pharmaceutically acceptable acid addition salt of the compound of the formula (I) includes a salt with an inorganic acid such as hydrochloride, hydrobromide, hydroiodide, sulfate, phosphate, etc., or a salt with an organic acid such as oxalate, maleate, fumarate, lactate, malate, citrate, tartrate, benzoate, methanesulfonate, succinate, etc. The compound of the formula (I) and a pharmaceutically acceptable acid addition salt thereof may exist in the form of a hydrate and/or a solvate, and the present invention also includes these hydrates and/or solvates as well.

The acid addition salt of the compound of the formula (II) or the formula (VIII) may be the above-mentioned pharmaceutically acceptable acid addition salts. The compound of the formula (II) or the formula (VIII) and an acid addition salt thereof may exist in the form of a hydrate and/or a solvate, and the present invention also includes these hydrates and/or solvates as well.

The compounds of the formula (I) and the formula (VIII) may optionally have one or more asymmetric carbon atoms, and by which stereoisomers thereof possibly exist, and the compounds of the formula (I) and the formula (VIII) may exist in a mixture of two or more stereoisomers. The present invention also includes these stereoisomers, a mixture thereof, and a racemic mixture thereof.

The terms used in the present specification are explained below.

The lower alkyl group and the lower alkyl moiety include a straight chain or branched chain alkyl group having 1 to 6 carbon atoms, unless defined otherwise.

The "halogen atom" is fluorine atom, chlorine atom, bromine atom, and iodine atom, and chlorine atom and bromine atom are preferable. The most preferable halogen atom is chlorine atom.

The "lower alkyl group" is, for example, methyl, ethyl, propyl, isopropyl, butyl, isobutyl, sec-butyl, t-butyl, pentyl, and hexyl.

The "cycloalkyl group" includes ones having 3 to 8 carbon atoms, for example, cyclopropyl, cyclobutyl, cyclopentyl, cyclohexyl, cycloheptyl, and cyclooctyl.

The "lower alkoxy group" includes an alkoxy group having 1 to 6 carbon atoms, for example, methoxy, ethoxy, propoxy, isopropoxy, butoxy, isobutoxy, sec-butoxy, t-butoxy, pentyloxy, and hexyloxy.

The "substituted or unsubstituted phenyl group" includes a phenyl group which may be substituted by one to three groups selected from the group consisting of a halogen atom, a $C_1$–$C_4$ alkyl group, a $C_1$–$C_4$ alkoxy group, a $C_1$–$C_4$ alkoxycarbonyl group, a trifluoromethyl group, an amino group, a mono- or di-$C_1$–$C_4$ alkylamino group, a cyano group and a nitro group, for example, phenyl; 2-, 3- or 4-chlorophenyl; 2-, 3- or 4-bromophenyl; 2-, 3- or 4-fluorophenyl; 2,4-dichlorophenyl; 2,4-dibromophenyl; 2,4-difluorophenyl; 2-, 3- or 4-methylphenyl; 2-, 3- or 4-methoxyphenyl; 4-trifluoromethylphenyl; 2-, 3- or 4-aminophenyl; 4-methylaminophenyl; 2-, 3- or 4-dimethylaminophenyl; 2-, 3- or 4-cyanophenyl; 2-, 3- or 4-nitrophenyl; and 4-amino-5-chloro-2-methoxyphenyl.

The "substituted or unsubstituted phenyl-lower alkyl group" includes an alkyl group having 1 to 4 carbon atoms which is substituted by the above-mentioned "substituted or unsubstituted phenyl group", for example, benzyl; 2-, 3- or 4-chlorobenzyl; 4-bromo-benzyl; 3- or 4-fluorobenzyl; 4-methylbenzyl; 4-methoxybenzyl; 1-phenethyl; and 2-phenethyl.

The "lower alkanoyl group" includes ones having 2 to 6 carbon atoms, for example, acetyl, propionyl, and butyryl.

The "lower alkoxycarbonyl group" includes ones having 1 to 6 carbon atoms in the alkoxy moiety, for example, methoxycarbonyl, ethoxycarbonyl, and propoxycarbonyl.

The "a lower alkyl group being substituted by a hydroxy, lower alkoxy or lower alkoxycarbonyl group" includes a lower alkyl group that is substituted by a hydroxy group, the above-mentioned "lower alkoxy group" or the above-mentioned "lower alkoxycarbonyl group", for example, methoxymethyl, 2-hydroxyethyl, 2-methoxyethyl, methoxycarbonylmethyl, ethoxycarbonylmethyl, 2-ethoxycarbonylethyl, 2-ethoxycarbonylpropyl, and 3-methoxycarbonylpropyl.

Among the compounds of the present invention, preferable one is a compound of the formula (I) wherein in the group of the formula (Ar-1), both $R^2$ and $R^3$ are hydrogen atoms, and $R^4$ is a methyl group, an ethyl group, a propyl group or an isopropyl group, or in the group of the formula (Ar-2), both $R^2$ and $R^3$ are hydrogen atoms, and $R^5$ and $R^6$ are both hydrogen atoms, or one of them is a methyl group, and the other is a hydrogen atom, and n is 1, and A is the same as defined above, and a pharmaceutically acceptable acid addition salt thereof.

More preferable compounds are compounds of the formula (I) wherein (a) in the formula (A-1), $Q^1$ is a hydrogen atom, a $C_1$–$C_4$ alkyl group, or a $C_3$–$C_7$ cycloalkyl group, $Q^2$ is a hydrogen atom, a $C_1$–$C_4$ alkyl group, a $C_3$–$C_7$ cycloalkyl group, a phenyl group being optionally substituted by a halogen, $C_1$–$C_4$ alkyl or $C_1$–$C_4$ alkoxy group, or a benzyl group being optionally substituted by the same substituents as above, or $Q^1$ and $Q^2$ may combine together with the nitrogen atom to which they bond to form a pyrrolidine ring, a piperidine ring, a hexahydroazepine ring, a morpholine ring, or a piperazine ring having optionally a $C_1$–$C_4$ alkyl or benzyl substituent on the other nitrogen atom, or (b) in the formula (A-2), $R^7$ is a hydrogen atom; a $C_1$–$C_4$ alkyl group; a $C_1$–$C_4$ alkyl group being substituted by a $C_1$–$C_4$ alkoxy or $C_1$–$C_4$ alkoxycarbonyl group; a $C_1$–$C_4$ alkoxy group; a $C_1$–$C_4$ alkoxycarbonyl group; or a phenyl group being optionally substituted by 1 to 3 groups selected from the group consisting of a halogen atom, a $C_1$–$C_4$ alkyl group, a $C_1$–$C_4$ alkoxy group and an amino group, or (c) in the formula (A-3), $R^8$ is a hydrogen atom or a $C_1$–$C_4$ alkyl group, $R^9$ is a $C_1$–$C_4$ alkyl group or a $C_1$–$C_4$ alkoxy group, and p is 0, 1 or 2, and $R^1$, $R^2$, $R^3$, $R^4$, $R^5$ and $R^6$ in the Ar are the same ones as those defined for the above-mentioned preferable compounds, and a pharmaceutically acceptable acid addition salt thereof.

Further preferable compounds are compounds of the following formula (I-1) or the formula (I-1'), and a pharmaceutically acceptable acid addition salt thereof.

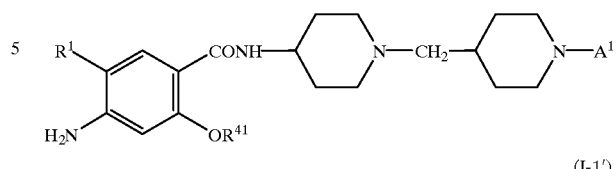

(I-1)

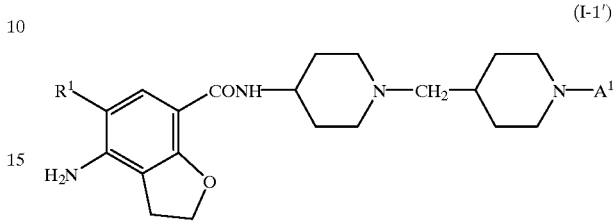

(I-1')

wherein $R^1$ is a halogen atom, $R^{41}$ is a methyl group, an ethyl group, a propyl group, or an isopropyl group, $A^1$ is a group of the following formula ($A^1$-1), ($A^1$-2) or ($A^1$-3):

$$-Z-N(Q^{11})(Q^{21})$$ ($A^1$-1)

(in which Z is —CO—, —CS— or —SO$_2$—, $Q^{11}$ and $Q^{21}$ are the same or different and each a methyl group, an ethyl group, a propyl group, or an isopropyl group, or $Q^{11}$ is a hydrogen atom, and $Q^{21}$ is a cyclopentyl group, a cyclohexyl group, a cycloheptyl group, or a substituted or unsubstituted phenyl group (said substituents may be a halogen atom, a $C_1$–$C_4$ alkyl group or a $C_1$–$C_4$ alkoxy group), or $Q^{11}$ and $Q^{21}$ may combine together with the nitrogen atom to which they bond to form a pyrrolidine ring or a morpholine ring);

$$-CO-R^{71}$$ ($A^1$-2)

(in which $R^{71}$ is a hydrogen atom, a methyl group, an ethyl group, a propyl group, a methoxy group, an ethoxy group, a $C_1$–$C_4$ alkyl group being substituted by a methoxy, ethoxy, methoxycarbonyl, or ethoxycarbonyl group, or a substituted or unsubstituted phenyl group (said substituents may be 1 to 3 groups selected from a halogen atom, a $C_1$–$C_4$ alkyl group, a $C_1$–$C_4$ alkoxy group and an amino group);

$$-(CH_2)_{p'}-CH(R^{81})-COR^{91}$$ ($A^1$-3)

(in which p' is 0, 1 or 2, $R^{81}$ is a hydrogen atom, a methyl group, or an ethyl group, $R^{91}$ is a methyl group, an ethyl group, a methoxy group, or an ethoxy group).

Especially preferable compounds are compounds of the following formula (I-2), or a pharmaceutically acceptable acid addition salt thereof, (I-2)

wherein $R^{11}$ is a chlorine atom or a bromine atom, $R^{41}$ is a methyl group, an ethyl group, a propyl group, or an isopropyl group, $R^{82}$ is a hydrogen atom, a methyl group, or an ethyl group, $R^{92}$ is a methyl group, an ethyl group, or an ethoxy group, and p" is 0, 1 or 2, compounds of the following formula (I-3), or a pharmaceutically acceptable acid addition salt thereof,

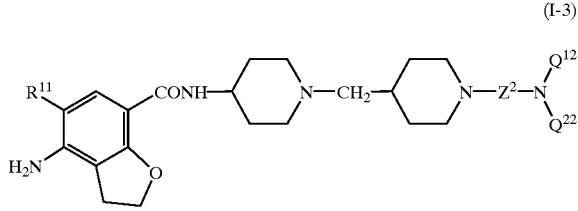
(I-3)

wherein $R^{11}$ is a chlorine atom or a bromine atom, $Z^2$ is —CO— or —CS—, $Q^{12}$ is a hydrogen atom, a methyl group, or an ethyl group, $Q^{22}$ is a methyl group, an ethyl group, or a phenyl group, or $Q^{12}$ and $Q^{22}$ may combine together with the nitrogen atom to which they bond to form a pyrrolidine ring, or compounds of the following formula (I-4), or a pharmaceutically acceptable acid addition salt thereof,

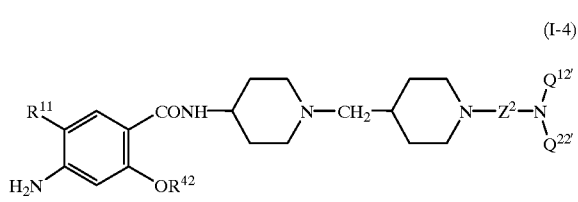
(I-4)

wherein $R^{11}$ is a chlorine atom or a bromine atom, $R^{42}$ is a methyl group, an ethyl group, or an isopropyl group, $Z^2$ is —CO— or —CS—, $Q^{12'}$ is a hydrogen atom, a methyl group, or an ethyl group, $Q^{22'}$ is a methyl group, an ethyl group, or a phenyl group, or $Q^{12'}$ and $Q^{22'}$ may combine together with the nitrogen atom to which they bond to form a pyrrolidine ring.

Preferable example of the compound of the formula (I-2) is the following compound, and a pharmaceutically acceptable acid addition salt thereof.

4-amino-5-chloro-2-methoxy-N-[1-[1-(2-butanon-3-yl)-4-piperidinylmethyl]-4-piperidinyl]benzamide (Compound of Example 84)

Preferable examples of the compound of the formula (I-3) are the following compounds, and a pharmaceutically acceptable acid addition salt thereof.

4-amino-5-chloro-N-[1-(1-dimethylcarbamoyl-4-piperidinylmethyl)-4-piperidinyl]-2,3-dihydrobenzo[b]furan-7-carboxamide (Compound of Example 18);

4-amino-5-chloro-N-[1-(1-diethylcarbamoyl-4-piperidinylmethyl)-4-piperidinyl]-2,3-dihydrobenzo[b]furan-7-carboxamide (Compound of Example 19);

4-amino-5-chloro-N-[1-(1-dimethylthiocarbamoyl-4-piperidinylmethyl)-4-piperidinyl]-2,3-dihydrobenzo[b]furan-7-carboxamide (Compound of Example 20);

4-amino-5-chloro-N-[1-[1-(1-pyrrolidinecarbonyl)-4-piperidinylmethyl]-4-piperidinyl]-2,3-dihydrobenzo[b]furan-7-carboxamide (Compound of Example 21); and 4-amino-5-chloro-N-[1-(1-phenylcarbamoyl-4-piperidinylmethyl)-4-piperidinyl]-2,3-dihydrobenzo[b]furan-7-carboxamide (Compound of Example 52).

Preferable examples of the compound of the formula (I-4) are the following compounds, and a pharmaceutically acceptable acid addition salt thereof.

4-amino-5-chloro-N-[1-(1-dimethylcarbamoyl-4-piperidinylmethyl)-4-piperidinyl]-2-methoxybenzamide (Compound of Example 1);

4-amino-5-chloro-N-[1-[1-(N-ethyl-N-methylcarbamoyl)-4-piperidinylmethyl]-4-piperidinyl]-2-methoxybenzamide (Compound of Example 4);

4-amino-5-chloro-2-methoxy-N-[1-[1-(N-methyl-N-phenylcarbamoyl)-4-piperidinylmethyl]-4-piperidinyl]benzamide (Compound of Example 8);

4-amino-5-chloro-N-[1-(1-dimethylthiocarbamoyl-4-piperidinylmethyl)-4-piperidinyl]-2-methoxybenzamide (Compound of Example 10);

4-amino-5-chloro-2-methoxy-N-[1-[1-(1-pyrrolidinecarbonyl)-4-piperidinylmethyl]-4-piperidinyl]benzamide (Compound of Example 12);

4-amino-5-chloro-N-[1-(1-dimethylcarbamoyl-4-piperidinylmethyl)-4-piperidinyl]-2-ethoxybenzamide (Compound of Example 25);

4-amino-5-bromo-N-[1-(1-dimethylcarbamoyl-4-piperidinylmethyl)-4-piperidinyl]-2-methoxybenzamide (Compound of Example 26);

4-amino-5-chloro-N-[1-(1-diethylcarbamoyl-4-piperidinylmethyl)-4-piperidinyl]-2-ethoxybenzamide (Compound of Example 27);

4-amino-5-chloro-N-[1-(1-dimethylcarbamoyl-4-piperidinylmethyl)-4-piperidinyl]-2-isopropoxybenzamide (Compound of Example 30);

4-amino-5-bromo-2-methoxy-N-[1-[1-(1-pyrrolidinecarbonyl)-4-piperidinylmethyl]-4-piperidinyl]benzamide (Compound of Example 34); and 4-amino-5-chloro-2-methoxy-N-[1-(1-phenylcarbamoyl-4-piperidinylmethyl)-4-piperidinyl]benzamide (Compound of Example 37).

Both $R^{41}$ and $R^{42}$ in the above formulae (I-2) and (I-4) are most preferably methyl groups.

Preferable intermediate (II) and preferable intermediate (VIII) are ones corresponding to the preferable compounds of the desired final compounds (I). Thus, the examples of especially preferable intermediate (II) are the following compounds and an acid addition salt thereof.

4-amino-5-chloro-2-methoxy-N-[1-(4-piperidinylmethyl)-4-piperidinyl]benzamide;

4-amino-5-bromo-2-methoxy-N-[1-(4-piperidinylmethyl)-4-piperidinyl]benzamide;

4-amino-5-chloro-2-ethoxy-N-[1-(4-piperidinylmethyl)-4-piperidinyl]benzamide; and 4-amino-5-chloro-N-[1-(4-piperidinylmethyl)-4-piperidinyl]-2,3-dihydrobenzo[b]furan-7-carboxamide.

In addition, the examples of especially preferable intermediates (VIII) are the following compounds, and an acid addition salt thereof.

4-amino-1-(1-dimethylcarbamoyl-4-piperidinylmethyl)piperidine;

4-amino-1-(1-dimethylthiocarbamoyl-4-piperidinylmethyl)piperidine; and 4-amino-1-[1-(1-pyrrolidinecarbonyl)-4-piperidinylmethyl]piperidine.

The examples of the intermediate (VIII) being included within the present invention are, in addition to the above-mentioned preferable compounds, the following compounds and an acid addition salt thereof, as well as compounds disclosed in Examples hereinafter.

4-amino-1-(1-diethylcarbamoyl-4-piperidinylmethyl) piperidine; and 4-amino-1-(1-phenylcarbamoyl-4-piperidinylmethyl) piperidine.

BEST MODE FOR CARRYING OUT THE INVENTION

The compounds of the present invention may be prepared, for example, by the following processes.

Process (a)

The compound of the formula (I) wherein A is a group of the formula (A-1) may be prepared by reacting a compound of the formula (II):

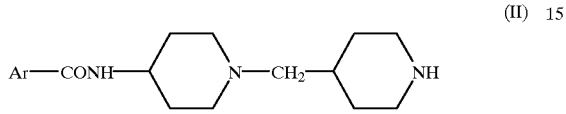

(II)

wherein Ar is the same as defined above, with a compound of the formula (III):

<div style="text-align:center">X—Z—N(Q$^1$)(Q$^2$)      (III)</div> wherein X is a halogen atom, Z, $Q^1$ and $Q^2$ are the same as defined above.

The halogen atom represented by X is a chlorine atom, a bromine atom or a iodine atom, but the most preferable one is a chlorine atom.

The reaction of the compound (II) with the compound (III) is carried out in a solvent or without a solvent. The solvent should be selected according to the types of the starting compounds, etc., and includes, for example, aromatic hydrocarbons (e.g., benzene, toluene, xylene), ethers (e.g., diethyl ether, tetrahydrofuran, dioxane), halogenated hydrocarbons (e.g., methylene chloride, chloroform), ketones (e.g., acetone, methyl ethyl ketone), ethyl acetate, acetonitrile, dimethylformamide, and dimethylsulfoxide. These solvents may be used alone or in the form of a mixture of two or more solvents.

The reaction may optionally be carried out in the presence of a base, if necessary. The base includes, for example, an alkali metal hydroxide (e.g., sodium hydroxide, potassium hydroxide), an alkali metal carbonate (e.g., sodium carbonate, potassium carbonate), an alkali metal hydrogen carbonate (e.g., sodium hydrogen carbonate, potassium hydrogen carbonate), and organic bases (e.g., triethylamine, tributylamine, diisopropylethylamine, N-methylmorpholine), but an excess amount of the compound (II) may be used instead of a base. The reaction temperature varies according to the types of the starting compounds to be used, but it is usually in the range of about −20° C. to about 150° C., preferably in the range of about −10° C. to about 80° C.

The process for preparing the intermediate of the formula (II) is explained below.

The compound of the formula (II) may be prepared by processes as shown in the following Chart 1 and Chart 2.

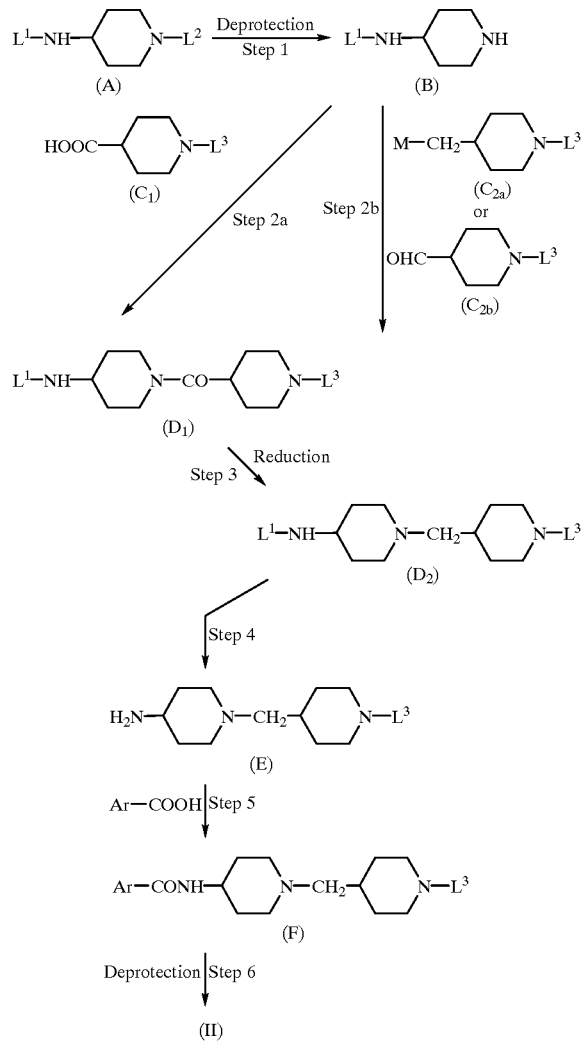

wherein $L^1$, $L^2$ and $L^3$ are protecting groups, but $L^1$ and $L^2$, and $L^1$ and $L^3$ are each a protecting group to be removed under different conditions, M is an alcoholic reactive ester residue, and Ar is the same as defined above.

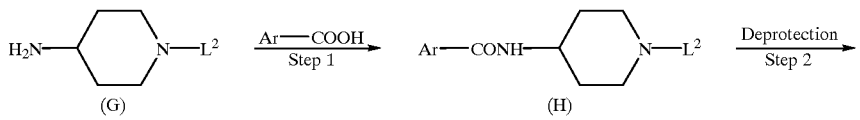

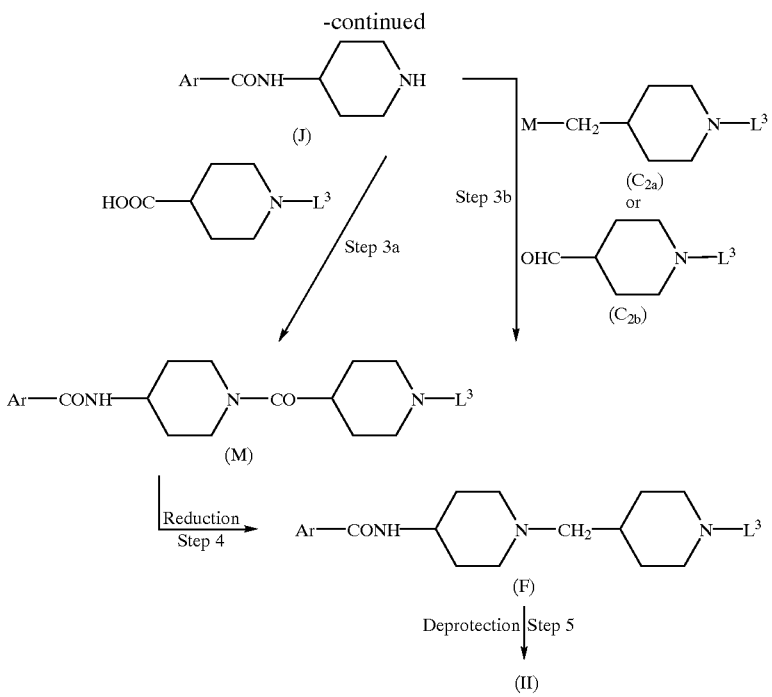

wherein Ar, $L^2$, $L^3$ and M are the same as defined above.

REMOVAL OF PROTECTING GROUPS

In Chart 1 and Chart 2, the protecting groups represented by $L^2$ and $L^3$ may be any protecting groups being able to easily be removed by hydrolysis or hydrogenolysis. The protecting group being able to be removed by hydrolysis includes, for example, ethoxycarbonyl group, t-butoxycarbonyl group, acetyl group, benzoyl group, trifluoroacetyl group, benzyloxycarbonyl group, 3- or 4-chlorobenzyloxycarbonyl group, triphenylmethyl group, methanesulfonyl group, p-toluenesulfonyl group, etc., and the protecting group being able to be removed by hydrogenolysis includes, for example, benzyloxycarbonyl group, 3- or 4-chlorobenzyloxycarbonyl group, benzylsulfonyl group, etc.

The removal of protecting group by hydrolysis is carried out by a conventional method, for example, by contacting with water under acid or basic conditions in a suitable solvent. The solvent includes, for example, alcohols (e.g., methanol, ethanol, isopropanol), acetone, dioxane, water, and a mixture of these solvents. The acid includes, for example, inorganic acids (e.g., hydrochloric acid, hydrobromic acid, hydroiodic acid, sulfuric acid), and organic acids (e.g., formic acid, acetic acid, trifluoroacetic acid, p-toluenesulfonic acid, methanesulfonic acid). The base includes, for example, an alkali metal hydroxide (e.g., sodium hydroxide, potassium hydroxide), and an alkali metal carbonate (e.g., sodium carbonate, potassium carbonate). The reaction is usually carried out at a temperature from about 0° C. to 150° C.

The removal of protecting group by hydrogenolysis is carried out by a conventional method, for example, by reacting in the presence of a catalyst (e.g., palladium-on-carbon, Raney-nickel, etc.), and hydrogen gas or a hydrogen donor (e.g., ammonium formate, cyclohexene, etc.) in a suitable solvent. The solvent includes, for example, alcohols (e.g., ethanol, methanol), water, acetic acid, dioxane, tetrahydrofuran, ethyl acetate, and dimethylformamide. The reaction is usually carried out at a temperature from about 0° C. to about 80° C., under atmospheric pressure or under pressure.

On the other hand, the protecting group represented by $L^1$ may be the same ones as those exemplified as the protecting group for $L^2$ and $L^3$, but $L^1$ and $L^2$ should be ones removed under different conditions, and $L^1$ and $L^3$ should also be ones removed under different conditions.

Reduction

The reduction reactions of Step 3 in Chart 1, and of Step 4 of Chart 2 are carried out by using a suitable reducing agent. That is, the reducing agent used in the present invention includes, for example, diborane, lithium aluminum hydride, an alkoxy-complex thereof, or a transition metal salt thereof, and sodium borohyride being added thereto aluminum chloride, boron trifluoride, phosphorus oxychloride or carboxylic acid (e.g., acetic acid, trifluoroacetic acid). The reduction reaction is carried out in a solvent such as ethers (e.g., diethyl ether, tetrahydrofuran, dimethoxyethane, dioxane, diglyme), toluene, chloroform, and methylene chloride, which should be selected according to the kinds of the reducing agent to be used. The reaction temperature may vary according to the kinds of the reducing agent to be used, but it is usually in the range of about 0° C. to about 160° C., preferably in the range of about 10° C. to 80° C.

Alkylation Reaction

The alkylation reactions using the compound of the formula $C_{2a}$ of Step 2b in Chart 1, and of Step 3b in Chart 2, are carried out in a solvent or without a solvent. The solvent should be selected according to the kinds of the starting compounds to be used, and includes, for example, aromatic hydrocarbons (e.g., benzene, toluene, xylene), ethers (e.g., diethyl ether, tetrahydrofuran, dioxane), halogenated hydrocarbons (e.g., methylene chloride, chloroform), alcohols (e.g., ethanol, isopropanol), ketones (e.g., acetone, methyl ethyl ketone), ethyl acetate, acetonitrile, dimethylformamide, dimethylsulfoxide, ethylene glycol, and these solvents may be used alone or in the form of a mixture of two or more solvents.

The reaction is carried out in the presence of a base, if necessary. The base includes, for example, an alkali metal hydroxide (e.g., sodium hydroxide, potassium hydroxide), an alkali metal carbonate (e.g., sodium carbonate, potassium carbonate), an alkali metal hydrogen carbonate (e.g., sodium hydrogen carbonate, potassium hydrogen carbonate), and organic bases (e.g., triethylamine, tributylamine, diisopropylethylamine, N-methylmorpholine), but an excess amount of amine which is a substrate for alkylation reaction may be used instead of a base.

The alcoholic reactive ester residue represented by M may be a halogen atom (e.g., chlorine, bromine, iodine), a lower alkylsufonyloxy group (e.g., methanesulfonyloxy), and an arylsulfonyloxy group (e.g., benzenesulfonyloxy, p-toluenesulfonyloxy), and a halogen atom, especially a chlorine atom, or methanesulfonyloxy and p-toluenesulfonyloxy are more preferable.

When M is a chlorine atom or a bromine atom, then the reaction can smoothly proceed by addition of an alkali metal iodide such as sodium iodide, potassium iodide. The reaction temperature varies according to the kinds of the starting compounds to be used, but it is usually in the range of about 0° C. to about 200° C., preferably in the range of about 20° C. to about 150° C.

Besides, the reductive alkylation reactions using the compound of the formula $C_{2b}$ of Step 2b in Chart 1 and of Step 3b in Chart 2 are carried out by catalytic reduction using platinum dioxide as a catalyst in the presence of a catalytic amount of an acid, or in the presence of a borane complex (e.g., pyridine borane, triethyl borane) or sodium cyanoborohydride. The solvent is the same as those defined for the above-mentioned alkylation reaction using the compound of the formula $C_{2a}$. The acid may be p-toluenesulfonic acid, etc. The reaction is usually carried out at a temperature from about 0° C. to about 100° C., preferably at a temperature from about 20° C. to about 80° C.

Amidation Reaction

The amidation reactions of Step 2a and Step 5 in Chart 1, and of Step 1 and Step 3a in Chart 2 are carried out by the method disclosed in Process (d) as described below.

On the other hand, the compound of the formula (III) may be commercially available ones or may be prepared by a conventional method.

Process(b)

The compound of the formula (I) wherein A is a group of the formula (A-1), $Q^1$ is a hydrogen atom, and Z is —CO— or CS— may be prepared by reacting a compound of the formula (II):

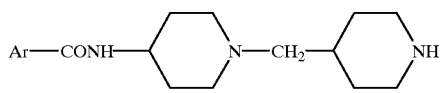
(II)

wherein Ar is the same as defined above, with a compound of the formula (IVa) or (IVb):

 (IVa)

 (IVb)

wherein $Q^{23}$ is the same substituents as those defined for the above $Q^2$, or a trimethylsilyl group).

The reaction of the compound (II) with the compound (IVa) or (IVb) is carried out in a solvent or without a solvent. The solvent should be selected according to the kinds of the starting compounds to be used, but may be the same as those defined for the above Process (a). When $Q^{23}$ is a trimethylsilyl group, said trimethylsilyl group is made free during the treatment after the reaction, and as a result, there is obtained a compound of the formula (I) wherein $Q^1$ and $Q^2$ are both hydrogen atoms.

The compounds of the formulae (IVa) and (IVb) are commercially available ones, or may be prepared by a conventional method.

Process (c)

The compound of the formula (I) wherein A is a group of the formula (A-1), and Z is —CO— is prepared by reacting a compound of the formula (V):

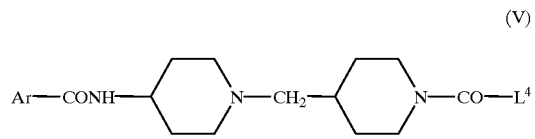
(V)

wherein $L^4$ is a leaving group, and Ar is the same as defined above, with a compound of the formula (VI):

 (VI)

wherein $Q^1$ and $Q^2$ are the same as defined above.

The reaction of the compound (V) with the compound (VI) is carried out in a solvent or without a solvent. The solvent should be selected according to the kinds of the starting compounds to be used, and may be the same solvents as those defined for the above-mentioned Process (a). The reaction temperature varies according to the kinds of the starting compounds to be used, but it is usually in the range of about 0° C. to about 250° C., preferably in the range of about 25° C. to about 200° C.

The compound (V) can be prepared by reacting the compound (II) with N,N'-carbonyldiimidazole, phosgene, diphosgene, triphosgene, di-(2-pyridyl) carbonate, N,N'-disuccinimidyl carbonate, bis(4-nitrophenyl) carbonate, bis (trichloromethyl) carbonate, phenoxycarbonyltetrazole, phenyl chlorocarbonate, chloromethyl chlorocarbonate, 2,4, 5-trichlorophenyl chlorocarbonate, trichloromethyl chlorocarbonate, 1-chloroethyl chlorocarbonate, 1,2,2,2-tetrachloroethyl chlorocarbonate, norborun-5-ene-2,3-dicarboxyimidyl chlorocarbonate, etc., in the presence of a base. The reaction is carried out in the same solvent under the same reaction conditions as those defined for Process (a).

The compound of the formula (I) wherein Z is —CO— may also be prepared by reacting a chloromethylcarbamate compound, which is obtained by reacting chloromethyl chlorocarbonate with the compound of the formula (VI) according to the method disclosed in Synth. Commun., 1996, 26, 4253, with the compound of the formula (II) in the same manner as in the preparation of the compound (V) as mentioned above. In this reaction, an alcohol such as ethanol can be used as a solvent, and the detailed procedures thereof are explained in Example 37 as described below.

Process (d)

The compound of the formula (I) is prepared by reacting a compound of the formula (VII):

 (VII)

wherein Ar is the same as defined above, or a reactive derivative thereof, with a compound of the formula (VIII):

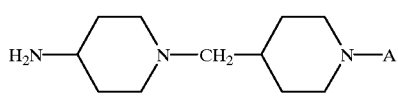
(VIII)

wherein A is the same as defined above.

The reactive derivative of the compound (VII) includes, for example, a lower alkyl ester (especially, a methyl ester), an active ester, an acid anhydride, and an acid halide (especially, an acid chloride). The active ester includes, for example, p-nitrophenyl ester, pentachlorophenyl ester, pentafluorophenyl ester, N-hydroxysuccinimide ester, N-hydroxyphthalimide ester, 1-hydroxybenzotriazole ester, 8-hydroxyquinoline ester, and 2-hydroxyphenyl ester. The acid anhydride includes, for example, a symmetric acid anhydride and a mixed acid anhydride. The mixed acid anhydride includes, for example, a mixed acid anhydride with an allyl chlorocarbonate such as ethyl chlorocarbonate and isobutyl chlorocarbonate, a mixed acid anhydride with an aralkyl chlorocarbonate such as benzyl chlorocarbonate, a mixed acid anhydride with an aryl chlorocarbonate such as phenyl chlorocarbonate, and a mixed acid anhydride with an alkanoic acid such as isovaleric acid and pivalic acid.

When the compound (VII) per se is used, the reaction can be carried out in the presence of a condensing agent such as 1,3-dicyclohexylcarbodiimide, 1-ethyl-3-(3-dimethylaminopropyl)carbodiimide hydrochloride, N,N'-carbonyldiimidazole, benzotriazol-1-yloxy-tris-(dimethylamino)phosphonium hexafluorophosphate, N,N'-carbonyldisuccinimide, 1-ethoxycarbonyl-2-ethoxy-1,2-dihydroquinoline, diphenylphosphoryl azide, and propanephosphonic anhydride. When 1,3-dicyclohexylcarbodiimide or 1-ethyl-3-(3-dimethylaminopropyl)carbodiimide hydrochloride is used as a condensing agent, N-hydroxysuccinimide, 1-hydroxybenzotriazole, 3-hydroxy-1,2,3-benzotriazin-4 (3H)-one, or N-hydroxy-5-norbornen-2,3-dicarboxyimide may be added into the reaction system.

The reaction of the compound (VII) or a reactive derivative thereof with the compound (VIII) is carried out in a solvent or without a solvent. The solvent varies according to the kinds of the starting compounds, etc., and includes, for example, aromatic hydrocarbons (e.g., benzene, toluene, xylene), ethers (e.g., diethyl ether, tetrahydrofuran, dioxane), halogenated hydrocarbons (e.g., methylene chloride, chloroform), ketones (e.g., acetone, methyl ethyl ketone), ethyl acetate, acetonitrile, dimethylformamide, dimethylsulfoxide, and these solvents may be used alone, or in the form of a mixture of two or more solvents.

The reaction may optionally be carried out in the presence of a base, if necessary. The base includes, for example, an alkali metal hydroxide (e.g., sodium hydroxide, potassium hydroxide), an alkali metal carbonate (e.g., sodium carbonate, potassium carbonate), an alkali metal hydrogen carbonate (e.g., sodium hydrogen carbonate, potassium hydrogen carbonate), and organic bases (e.g., triethylamine, tributylamine, diisopropylethylamine, N-methylmorpholine), but an excess amount of the compound (VIII) may be used instead of a base.

The reaction temperature varies according to the kinds of the starting compounds, but it is usually in the range of about −30° C. to about 200° C., preferably in the range of about −10° C. to about 150° C.

The compound (VIII) is prepared by the process as shown in Chart 3 as described below.

Chart 3

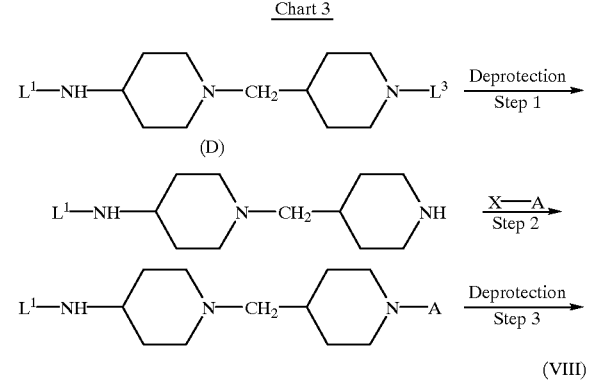

(VIII)

wherein $L^1$, $L^3$, X and A are the same as defined above.

Step 2 in Chart 3 is carried out in the same manner as in Process (a), and Step 1 and Step 3 in Chart 3 are carried out in the same manner as in the process of the removal of protecting group as mentioned above.

Process (e)

The compound of the formula (I) wherein A is the group of the formula (A-2) is prepared by reacting a compound of the formula (II):

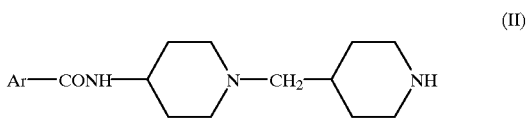

wherein Ar is the same as defined above, with a compound of the formula (A-2'):

wherein $R^{72}$ is the same as $R^7$, or a reactive derivative thereof, provided that when (1) $R^{72}$ is a lower alkyl group substituted by a hydroxy group, then a reactive derivative of the compound (A-2') is not used, and when (2) $R^{72}$ is a lower alkoxy group, then an acid halide of the compound (A-2') is used.

The reaction of the compound (A-2') or a reactive derivative thereof with the compound (II) is carried out in a solvent or without a solvent.

The reactive derivative of the compound (A-2') may be the same ones as those defined for Process (d). Besides, when the compound (A-2') per se is used, the reaction may be carried out in the presence of the same condensing agents as mentioned in Process (d). The solvent may be the same solvents as those defined for Process (d), but it should be selected according to the kinds of the starting compounds to be used. The reaction is also carried out in the presence of a base, if necessary. The base may be the same as those defined for Process (d), but an excess amount of the compound (II) may be used instead of a base. The reaction temperature varies according to the kinds of the starting compounds to be used, but it is usually in the range of about −30° C. to about 200° C., preferably in the range of about −10° C. to about 150° C.

The compound (A-2') may be commercially available ones, or can be prepared by a conventional method.

Process (f)

The compound of the formula (I) wherein A is a group of the formula (A-3) is prepared by reacting a compound of the formula (II):

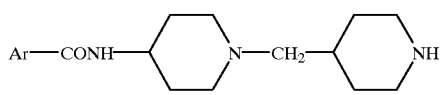
(II)

wherein Ar is the same as defined above, with a compound of the formula (A-3'):

M—(CH$_2$)p—CH(R$^8$)—COR$^9$ (A-3')

wherein M is an alcoholic reactive ester residue as mentioned above, and R$^8$, R$^9$ and p are the same as defined above, or with a compound of the formula (A-3"):

O=CH—(CH$_2$)p'—CH(R$^8$)—COR$^9$ (A-3")

wherein p' is 1, 2, 3 or 4, and R$^8$ and R$^9$ are the same as defined above.

The reaction of the compound (II) with the compound (A-3') is carried out in a solvent or without a solvent. The solvent should be selected according to the kinds of the starting compounds to be used, and includes, for example, aromatic hydrocarbons (e.g., benzene, toluene, xylene), ethers (e.g., diethyl ether, tetrahydrofuran, dioxane), halogenated hydrocarbons (e.g., methylene chloride, chloroform), alcohols (e.g., ethanol, isopropanol), ketones (e.g., acetone, methyl ethyl ketone), ethyl acetate, acetonitrile, dimethylformamide, dimethylsulfoxide, and ethylene glycol, and these solvents may be used alone, or in the form of a mixture of two or more solvents.

The reaction is also carried out in the presence of a base, if necessary. The base includes, for example, an alkali metal hydroxide (e.g., sodium hydroxide, potassium hydroxide), an alkali metal carbonate (e.g., sodium carbonate, potassium carbonate), an alkali metal hydrogen carbonate (e.g., sodium hydrogen carbonate, potassium hydrogen carbonate), and organic bases (e.g., triethylamine, tributylamine, diisopropylethylamine, N-methylmorpholine), but an excess amount of the compound (II) may be used instead of a base. When M is a chlorine atom or a bromine atom, the reaction can smoothly proceed by addition of an alkali metal iodide such as sodium iodide, potassium iodide. The reaction temperature varies according to the kinds of the starting compounds to be used, but it is usually in the range of about 0° C. to about 200° C., preferably in the range of about 80° C. to about 150° C.

The reaction of the compound (II) with the compound (A-3") is carried out in a solvent or without a solvent. The solvent should be selected according to the kinds of the starting compounds to be used, and may be the same as those mentioned above.

The reaction is carried out in the presence of a borane complex (e.g., pyridine borane, triethylamine borane), or sodium cyanoborohydride, or a catalyst such as platinum oxide under hydrogen atmosphere, and if necessary, in the presence of a catalytic amount of an acid such as p-toluenesulfonic acid, etc. The reaction temperature varies according to the kinds of the starting compounds to be used, but it is usually in the range of about 0° C. to about 100° C., preferably in the range of about 20° C. to about 180° C.

Moreover, an iminium salt compound, which is produced during the reaction of the compound (II) with the compound (A-3"), can be collected, and can be reduced by the above-mentioned method.

The compound (A-3') and the compound (A-3") may be commercially available ones, or can be prepared by a conventional method.

In addition, the compounds of the present invention can also be prepared by the following processes as well.

The compound of the formula (I) wherein A is a formyl group is prepared by a conventional formylization of the compound (II), and the detailed procedures thereof are explained in Example 79 as described below.

The desired compounds obtained in the above Processes can be isolated and purified by a conventional method such as chromatography, recrystallization, re-precipitation, etc.

The compound (I) can be obtained either in the form of a free base or in the form of an acid addition salt thereof, according to the kinds of starting compounds and reaction conditions. The acid addition salt can be converted into a free base by a conventional method, for example, by treating it with a base such as alkali metal carbonate, an alkali metal hydroxide. On the other hand, the compound (I) in the form of a free base can be converted into an acid addition salt thereof by treating with various acids in a conventional manner.

The pharmacological activities of the present compounds are explained by the following pharmacological experiments on the representative compounds of the present invention.

Experiment 1

Binding Assay on Serotonin 4 (5-HT$_4$) Receptors

5-HT$_4$ receptor binding assays and the preparation of receptor membrane fractions therefor were carried out according to a modified method of the method of Grossman et al. British J. Pharmacol., 1993, 109, 618–624.

Std-Hartley guinea pigs weighing 300–400 g were decapitated, and the brain thereof was immediately taken out, and the striatum was dissected. To the tissue thus obtained was added 15-times volume of Hepes buffer (50 mM, pH7.4, 4° C.), homogenized in a Teflon homogenizer, and centrifuged at 48,000×g at 4° C. for 15 minutes. The pellet was suspended in the same Hepes buffer in a volume of 1 ml per 30 mg of the wet tissues to give receptor membrane fractions.

In the assay tubes, the Hepes buffer (50 mM. pH 7.4, 4° C., 1 ml) containing 0.1 nM [$^3$H]-GR1 13808 (chemical name; [1-[2-(methylsulfonylamino)ethyl]-4-piperidinyl] methyl 1-methylindole-3-carboxylate), and the receptor membrane fraction, either test compound or 30 μM serotonin, was incubated at 37° C. for 30 minutes. The reaction was terminated by rapid vacuum filtration and washing (3×4 ml) with ice-cold 50 mM Tris-HCl buffer (pH 7.7) through Whatman GF/B filter paper using a Brandel cell harvester. Prior to the filtration, the filter to be used was presoaked in a 0.1% solution of polyethylenimine for one hour. The radioactivity on the filter was determined with by ACS-II scintillation cocktail by a liquid scintillation counter.

The concentration of the test compounds causing 50 % inhibition of specific binding of the [$^3$H]-GR113808 (IC$_{50}$ value) was determined by inhibitory rate of the test compound against the specific binding which was obtained by subtracting the non-specific binding from the total [$^3$H]-GR113808 binding. The results are shown in Table 1.

TABLE 1

Binding studies of serotonin 4 (5-HT$_4$) receptors

| Test Comp. | IC$_{50}$ (nM) | Test Comp | IC$_{50}$ (nM) |
|---|---|---|---|
| 1* | 11.9 | 42 | 6.4 |
| 2 | 11.9 | 47 | 1.6 |
| 3 | 15.5 | 49 | 4.4 |
| 4 | 11.9 | 51 | 1.9 |
| 5 | 7.6 | 52 | 0.36 |
| 8 | 6.3 | 53 | 9.8 |
| 10 | 8.0 | 60 | 3.9 |
| 11 | 6.8 | 61 | 4.6 |
| 12 | 8.7 | 62** | 1.4 |
| 13 | 19.1 | 63 | 20.7 |
| 16 | 14.2 | 69 | 18.0 |
| 18 | 3.3 | 72** | 6.8 |
| 19 | 2.7 | 73 | 4.2 |
| 20 | 1.3 | 74** | 9.0 |
| 21 | 2.4 | 81 | 7.7 |
| 25 | 4.2 | 84 | 14.2 |
| 26 | 11.5 | 85 | 18.2 |
| 27 | 4.4 | 86 | 8.3 |
| 30 | 4.3 | 87 | 11.9 |
| 32 | 3.2 | 88 | 7.2 |
| 33 | 2.3 | 89 | 6.5 |
| 34 | 8.9 | 92 | 4.1 |
| 37 | 1.1 | 98 | 12.5 |
| 38 | 1.6 | 99 | 3.9 |
| 39 | 2.3 | 100 | 1.0 |
| 40 | 1.7 | Comp. A | 23.0 |

*The compound of Example 1 (fumarate) (hereinafter, the test compound numbers mean fumarates of the compounds of the corresponding Examples except for the numbers marked by **)
**Free bases of the compound of the corresponding Examples
Comp. A: Cisapride

Experiment 2

Assay on Evacuation in Mice

Male mice of Std-ddY strain weighing 25–30 g were used. Free access to food and water was allowed up to the beginning of the procedure.

The mice (each group: five mice) were placed in a mesh bottom cage for fasting, and they were allowed for acclimation to new environment for about one hour prior to the start of the experiment. A test compound, which was previously suspended in the 0.5% tragacanth solution, was administered orally to the mice at a dose of 1 mg/kg. The fecal pellets were counted and collected at 30, 60 and 120 minutes after the treatment of a test compound, and weighed.

The statistical judgment of efficacy was carried out between the control group and the treated group, and determined by Dunnett's test.

−: Inactive
+: Moderately stimulated (P<0.05)
++: Markedly stimulated (p<0.01)

TABLE 2

Assay on evacuation in mice

| Test Comp. | Effect | Test Comp. | Effect |
|---|---|---|---|
| 1* | ++ | 30 | ++ |
| 2 | + | 32 | + |
| 4 | ++ | 34 | ++ |
| 8 | ++ | 37 | ++ |
| 10 | ++ | 52 | ++ |
| 12 | ++ | 64 | + |
| 18 | ++ | 75 | ++ |
| 19 | ++ | 76 | ++ |
| 20 | ++ | 77 | ++ |
| 21 | ++ | 79 | + |
| 25** | ++ | 81 | ++ |
| 26 | + | 86** | ++ |
| 27 | ++ | 90 | + |

*The compound of Example 1 (fumarate) (hereinafter, the test compound numbers mean a fumarate of the compound of the corresponding Examples except for the numbers marked with **)
**Free bases of the compound of the corresponding Examples

Experiment 3

Acute Toxity

Male mice of Std-ddY strain weighing 25–30 g were used in a group of 5 animals. A test compound was suspended in physiological saline solution or 1% lactose solution and administered intravenously to the mice. Then, the lethality of the mice was observed for 7 days after the treatment, and 50% lethal dose (LD$_{50}$) was determined. The LD$_{50}$ doses of the compounds of Examples 1, 10, 12, 18, 20, 21, 25 and 26 were all more than 100 mg/kg.

As is shown in the results of the above pharmacological experiments, the compounds of the present invention and a pharmaceutically acceptable acid addition salt thereof show a potent affinity for 5-HT$_4$ receptors, therefore, they are useful as a 5-HT$_4$ receptor agonist in the prophylaxis or treatment of diseases or disorders, which are caused by the lack of the stimulation of the 5-HT$_4$ receptors. For example, the compounds of the present invention and a pharmaceutically acceptable acid addition salt thereof can be used in the prophylaxis or treatment of gastrointestinal diseases, such as irritable bowel syndrome, flaccid constipation, habitual constipation, drug-induced constipation (e.g., constipation induced by morphine, a psychotropic), chronic diarrhea, infant diarrhea. The compounds of the present invention and a pharmaceutically acceptable acid addition salt thereof are also useful in the prophylaxis or treatment of gastrointestinal diseases such as acute or chronic gastritis, reflux esophagitis, gastric neurosis, paralytic ileus after surgery, senile ileus, postgastrectomy syndrome and intestinal pseudo-obstruction, as well as in the prophylaxis or treatment of anorexia, nausea, vomiting, abdominal fullness, upper abdominal discomfort, visceral pain, heartburn and eructation which are accompanied by the above mentioned gastrointestinal diseases, gastric or duodenal ulcer, scleroderma, diabetes, biliary duct disorders, etc. The compounds of the present invention and a pharmaceutically acceptable acid addition salt thereof are further useful in the prophylaxis or treatment of central nervous disorders such as schizophrenia, depression, disturbance of memory, anxiety, etc., urinary diseases such as dysuria accompanied by urinary obstruction or prostatomegaly. Therefore, the compounds of the present invention and a pharmaceutically acceptable acid addition salt thereof can be used in the prophylaxis or treatment of the above-mentioned various diseases, especially of gastrointestinal diseases, or various gastrointestinal dysfunction accompanied by the treatment of the above-mentioned various diseases, and hence, they are especially useful as a gastrointestinal motility enhancer or as a gastrointestinal prokinetic agent.

The compounds of the present invention can be administered either orally, parenterally or rectally. The dose of the compounds of the present invention varies according to the kinds of the compound, the administration routes, the conditions, ages of the patients, etc., but it is usually in the range of 0.01–30 mg/kg/day, preferably in the range of 0.05–10 mg/kg/day.

The compounds (I) of the present invention and a pharmaceutically acceptable acid addition salt thereof are usually administered in the form of a pharmaceutical preparation, which is prepared by mixing thereof with a pharmaceutically acceptable carrier or diluent. The pharmaceutically acceptable carrier or diluent may be any conventional ones being usually used in the pharmaceutical field, and do not react with the compounds of the present invention. Suitable examples of the pharmaceutically acceptable carrier or diluent are, for example, lactose, inositol, glucose, mannitol, dextran, sorbitol, cyclodextrin, starch, partly pregelatinized starch, white sugar, magnesium metasilicate aluminate, synthetic aluminum silicate, crystalline cellulose, sodium carboxymethylcellulose, hydroxypropyl starch, calcium carboxylmethylcellulose, ion exchange resin, methylcellulose, gelatin, gum arabic, pullulan, hydroxypropyl cellulose, low substituted hydroxypropyl cellulose, hydroxypropylmethylcellulose, polyvinylpyrrolidone, polyvinyl alcohol, alginic acid, sodium alginate, light anhydrous silicic acid, magnesium stearate, talc, tragacanth, bentonite, veegum, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, water, propyleneglycol, ethanol, sodium chloride, sodium hydroxide, hydrochloric acid, citric acid, benzyl alcohol, glutamic acid, glycine, methyl p-hydroxybenzoate, propyl p-hydroxybenzoate, etc.

The pharmaceutical preparation is, for example, tablets, capsules, granules, powders, syrups, suspensions, injection preparations, suppositories, nasal drops, sublingual preparations, etc. These preparations may be prepared by a conventional method. In the preparation of liquids, the compound of the present invention may be dissolved or suspended in water or a suitable other solvent, when administered. Tablets and granules may be coated by a conventional method. In the injection preparations, it is preferable to dissolve the compound of the present invention in water, but if necessary, it may be dissolved by using an isotonic agent or a solubilizer, and further, a pH adjuster, a buffering agent or a preservative may be added thereto.

These preparations may contain the compound (I) of the present invention or a pharmaceutically acceptable acid addition salt thereof at a ratio of at least 0.01%, preferably at a ratio of 0.1–70%. These preparations may also contain other therapeutically effective compounds as well.

The present invention is illustrated in more detail by the following Reference Examples and Examples, but should not be construed to be limited thereto.

The identification of the compounds is carried out by Elemental analysis, Mass spectrum, IR spectrum, NMR spectrum, etc.

The following abbreviations may be used in the following Reference Examples and Examples in order to simplify the description.

Substituents

| | |
|---|---|
| Me: | Methyl group |
| Et: | Ethyl group |
| Pr: | Propyl group |
| iPr: | Isopropyl group |
| Bu: | Butyl group |
| iBu: | Isobutyl group |
| tBu: | t-Butyl group |
| Ph: | Phenyl group |

Solvent for recrystallization

| | |
|---|---|
| CF: | Chloroform |
| E: | Ethanol |
| EA: | Ethyl acetate |
| HX: | n-Hexane |
| M: | Methanol |
| MEK: | Methyl ethyl ketone |
| T: | Toluene |

NMR

| | |
|---|---|
| s: | Singlet |
| d: | Doublet |
| t: | Triplet |
| m: | Multiplet |
| brs: | Broad singlet |
| J: | Coupling constant |

REFERENCE EXAMPLE 1

Preparation of 1-[(1-benzyloxycarbonyl)-4-piperidinylmethyl]-4-(t-butoxycarbonylamino) piperidine (1) To a solution of 4-amino-1-benzylpiperidine (95 g) in chloroform (600 ml) is added dropwise a solution of di-t-butyl bicarbonate (109 g) in chloroform (600 ml) under ice-cooling. The mixture is stirred at room temperature for 5 hours, and washed twice with water, and washed with a saturated aqueous sodium chloride solution. The solution is dried over anhydrous magnesium sulfate, and the solvent is evaporated under reduced pressure. To the residue thus obtained is added petroleum ether, and the insoluble solid is collected by filtration, and dried to give 1-benzyl-4-(t-butoxycarbonylamino) piperidine (136 g) as a solid.

(2) To a solution of the above product (70 g) and ethanol (600 ml) is added 10% palladium-on-carbon (5 g), and the mixture is hydrogenated at 40° C. under atmospheric pressure. After a theoretical amount of hydrogen is consumed, the catalyst is removed by filtration, and the filtrate is concentrated under reduced pressure to remove the ethanol to give 4-(t-butoxycarbonylamino)piperidine (48.6 g) as a solid.

M.p. 155–158° C.

(3) To a solution of 1-benzyloxycarbonyl-4-piperidinecarboxylic acid (26 g) in methylene chloride (200 ml) is added dropwise thionyl chloride (14.4 ml) at room temperature. The mixture is heated under reflux for one hour, and the solvent and the excess amount of thionyl chloride are removed under reduced pressure. To the residue is added methylene chloride (400 ml), and thereto is added a mixture of the above obtained 4-(t-butoxycarbonylamino)piperidine (20 g) and triethylamine (27 ml) under ice-cooling. The mixture is stirred at room temperature for 4 hours, and washed successively with water, a 10% aqueous citric acid solution, water, a saturated aqueous sodium hydrogen carbonate solution, and a saturated aqueous sodium chloride solution, and dried over anhydrous magnesium sulfate. The solvent is evaporated under reduced pressure to give 1-(1-benzyloxycarbonyl-4-piperidinylcarbonyl)-4-(t-butoxycarbonylamino)piperidine (39 g) as a solid.

M.p. 150–152° C. (recrystallized from ethyl acetate)

(4) To a suspension of the above product (16.5 g) in tetrahydrofuran (170 ml) is added dropwise a 1M solution of borane tetrahydrofuran complex in tetrahydrofuran (100 ml) under ice-cooling, and the mixture is stirred at room temperature for 13 hours. To the reaction mixture is added dropwise methanol (100 ml), and the mixture is heated under reflux for one hour. The solvent is evaporated under reduced pressure, and the resulting residue is dissolved in ethyl acetate. The solution is washed successively with water, an aqueous sodium hydroxide solution, and a saturated aqueous sodium chloride solution, and dried over anhydrous sodium sulfate. The solvent is evaporated under reduced pressure, and the residue is purified by silica gel flash column chromatography (eluent; ethyl acetate) to give the desired compound (13 g) as a solid.

M.p. 130–132° C. (recrystallized from ethyl acetate)

REFERENCE EXAMPLE 2

Preparation of 4-amino-1-(1-benzyloxycarbonyl-4-piperidinylmethyl)piperidine

To a solution of 1-(1-benzyloxycarbonyl-4-piperidinylmethyl)-4-(t-butoxycarbonylamino)piperidine (7.77 g) in ethanol (30 ml) is added a 30% solution of hydrochloric acid in ethanol (15 ml) under ice-cooling, and the mixture is stirred at room temperature for 5 hours. The solvent is evaporated under reduced pressure, and the residue is dissolved in water. The solution is basified with potassium carbonate and extracted with chloroform. The extract is washed with a saturated aqueous sodium chloride solution, dried over anhydrous magnesium sulfate, and the solvent is evaporated under reduced pressure to give the desired compound (6.04 g) as an oily product.

The examples for preparing the intermediate (II) and the intermediate (VIII) are shown in the following Examples A–D.

Example A

Preparation of 4-amino-1-(1-dimethylcarbamoyl-4-piperidinylmethyl)piperidine (1) To a solution of 1-(1-benzyloxycarbonyl-4-piperidinylmethyl)-4-(t-butoxycarbonylamino)piperidine (5.6 g) in ethanol (100 ml) is added 5% palladium-on-carbon (0.6 g), and the mixture is hydrogenated at 30° C. under atmospheric pressure. After a theoretical amount of hydrogen is consumed, the catalyst is removed by filtration, and the ethanol in the filtrate is evaporated under reduced pressure to give crude 4-(t-butoxycarbonylamino)-1-(4-piperidinylmethyl)piperidine (4.13 g).

(2) The above product and dimethylcarbamoyl chloride are treated in a similar manner as Example 1 as described below to give 4-(t-butoxycarbonylamino)-1-(1-dimethylcarbamoyl-4-piperidinylmethyl)piperidine.

$^1$H-NMR spectrum (CDCl$_3$, δ ppm): 1.12–2.18 (13H, m), 1.46 [9H, s, (CH$_3$)$_3$], 2.63–2.82 (4H, m), 2.80 [6H, s, (CH$_3$)$_2$], 3.42 (1H, m), 3.59–3.70 (2H, m), 4.42 (1H, d, J=8.2 Hz, NH)

(3) The above product is treated in a similar manner as in Reference Example 2 to give the desired compound.

Examples A1 and A2

The following compounds are prepared in a similar manner as in Example A-(2) and (3) except that the corresponding carbamoyl or thiocarbamoyl chlorides are used instead of dimethylcarbamoyl chloride in Example A-(2).

Example A1

4-Amino-1-(1-dimethylthiocarbamoyl-4-piperidinylmethyl)piperidine

Example A2

4-Amino-1-(1-pyrrolidinecarbonyl-4-piperidinylmethyl)piperidine

Example A3

Preparation of 4-amino-1-(1-methylcarbamoyl-4-piperidinylmethyl)piperidine:

(1) To a solution of diphosgene (160 mg) in methylene chloride (20 ml) is added dropwise a solution of pentafluorophenol (290 mg) in methylene chloride (10 ml) under ice-cooling, and the mixture is stirred at room temperature for one hour. To the reaction solution is added dropwise a solution of 4-(t-butoxycarbonylamino)-1-(4-piperidinylmethyl)piperidine (480 mg) and triethylamine (160 mg) in methylene chloride (10 ml) under ice-cooling, and the mixture is stirred at room temperature for 4 hours. The reaction mixture is washed with water and a saturated aqueous sodium chloride solution, dried over anhydrous magnesium sulfate, and the solvent is evaporated under reduced pressure. The residue is purified by silica gel column chromatography (eluent; chloroform:methanol=30:1) to give 4-(t-butoxycarbonylamino)-1-(1-pentafluorophenoxycarbonyl-4-piperidinylmethyl)piperidine (740 mg).

(2) To a solution of the above product (740 mg) in ethanol (10 ml) is added a 30% solution of methylamine in ethanol (1.51 g), and the mixture is stirred at room temperature for 8 hours, and the solvent is evaporated under reduced pressure. The residue is dissolved in chloroform, and the solution is washed with water and a saturated aqueous sodium chloride solution, dried over anhydrous magnesium sulfate, and the solvent is evaporated under reduced pressure. The residue is purified by silica gel column chromatography (eluent; chloroform:methanol=10:1) to give 4-(t-butoxycarbonylamino)-1-(1-methylcarbamoyl-4-piperidinylmethyl)piperidine (460 mg).

(3) The above product is treated in a similar manner as in Reference Example 2 to give the desired compound.

Example A4

Preparation of 4-amino-1-(1-carbamoyl-4-piperidinylmethyl)piperidine (1) To a solution of 4-(t-butoxycarbonylamino)-1-(4-piperidinylmethyl)piperidine (590 mg) in methylene chloride (30 ml) is added trimethylsilyl isocyanate (220 mg) under ice-cooling, and the mixture is stirred at room temperature for 8 hours. The reaction mixture is washed with water and a saturated aqueous sodium chloride solution, dried over anhydrous magnesium sulfate, and the solvent is evaporated under reduced pressure. The residue is purified by silica gel column chromatography (eluent; chloroform:methanol=10:1) to give 4-(t-butoxycarbonylamino)-1-(1-carbamoyl-4-piperidinylmethyl)piperidine (540 mg).

(2) The above product is treated in a similar manner as in Reference Example 2 to give the desired compound.

Example A5

Preparation of 4-amino-1-(1-methoxycarbonyl-4-piperidinylmethyl)piperidine

The desired compound is obtained in a similar manner as in Example 1 as described below and Reference Example 2 except that methyl chloroformate (=methyl chlorocarbonate) is used instead of dimethylcarbamoyl chloride in Example A-(2).

Example A6

Preparation of 4-amino-1-(1-piperidinecarbonyl-4-piperidinylmethyl)piperidine (1) Similar procedures as Example 1 are repeated except that phenyl chloroformate is used instead of dimethylcarbamoyl chloride in Example A-(2) to give 4-(t-butoxycarbonylamino)-1-(1-phenoxycarbonyl-4-piperidinylmethyl)piperidine.

(2) Similar procedures as Example 55 are repeated except that the above product and piperidine are used instead of 4-amino-5-chloro-2-methoxy-N-[1-(1-phenoxycarbonyl-4-piperidinylmethyl)-4-piperidinyl]-benzamide and pyrrolidine in Example 55 as described below, respectively, to give 4-(t-butoxycarbonylamino)-1-(1-piperidinecarbonyl-4-piperidinylmethyl)piperidine.

(3) The above product is treated in a similar manner as in Reference Example 2 to give the desired compound.

Example A7

Preparation of 4-amino-1-[1-(3-methoxypropionyl)-4-piperidinylmethyl)piperidine (1) Similar procedures as Example 60 are repeated except that 4-(t-butoxycarbonylamino)-1-(4-piperidinylmethyl)piperidine, and 3-methoxypropionic acid are used instead of 4-methoxybenzoic acid in Example 60 as described below to give 4-(t-butoxycarbonylamino)-1-[1-(3-methoxypropionyl)-4-piperidinylmethyl]piperidine.

(2) The above product is treated in a similar manner as in Reference Example 2 to give the desired compound.

Examples A8–A10

The following compounds are obtained in a similar manner as in Example 1 or 72 as described below and Reference Example 2 except that the corresponding starting compounds are used instead of dimethylcarbamoyl chloride in Example A-(2).

(Example A8)
4-Amino-1-[1-(1-morpholinecarbonyl)-4-piperidinylmethyl]piperidine
(Example A9)
4-Amino-1-(1-acetyl-4-piperidinylmethyl)piperidine
(Example A10)
4-Amino-1-(1-dimethylsulfamoyl-4-piperidinylmethyl)piperidine Example B Preparation of 4-amino-5-chloro-2-methoxy-N-[1-(4-piperidinylmethyl)-4-piperidinyl]benzamide (1) To 1-(1-benzyloxycarbonyl-4-piperidinylmethyl)-4-(t-butoxycarbonylamino)piperidine (12.1 g) is added a 10% solution of hydrochloric acid in ethanol (60 ml) under ice-cooling, and the mixture is stirred at room temperature for one hour, and the solvent is evaporated under reduced pressure. To the residue is added methylene chloride (100 ml), and then thereto are further added successively 4-amino-5-chloro-2-methoxybenzoic acid (5.3 g), 1-ethyl-3-(3-dimethylaminopropyl)carbodiimide hydrochloride (5.4 g), and triethylamine (27 ml) under ice-cooling, and the mixture is stirred at room temperature for 3 hours. The reaction mixture is washed successively with water, a saturated aqueous sodium hydrogen carbonate solution, water, and a saturated aqueous sodium chloride solution, dried over anhydrous magnesium sulfate, and the solvent is evaporated under reduced pressure. The residue is purified by silica gel flash column chromatography (eluent; chloroform:methanol=20:1) to give 4-amino-N-[1-(1-benzyloxycarbonyl-4-piperidinylmethyl)-4-piperidinyl]-5-chloro-2-methoxybenzamide (10.2 g).

(2) The above product is dissolved in chloroform (150 ml), and thereto are added anisole (19 ml), and methanesulfonic acid (11.5 ml), and the mixture is heated under reflux for 3 hours. The reaction mixture is allowed to cool, and most of the chloroform is removed by decantation. The residue is dissolved in water and washed with chloroform. The aqueous layer is basified with potassium carbonate and extracted with chloroform. The extract is washed with a saturated aqueous sodium chloride solution, dried over anhydrous magnesium sulfate, and the solvent is evaporated under reduced pressure to give the crude desired compound, which is further treated with fumaric acid by a conventional method to give the difumarate of the desired compound.

M.p. 187–189° C. (recrystallized from ethanol)

$^1$H-NMR spectrum (CDCl$_3$, δ ppm): 1.00–1.17 (2H, m), 1.43–2.20 (12H, m), 2.53–2.67 (2H, m), 2.68–2.80 (2H, m), 3.02–3.10 (2H, m), 3.88 (3H, s, OCH$_3$), 3.99 (1H, m), 4.39 (2H, s, NH$_2$), 6.29 (1H, s, Ph-H), 7.64 (1H, d, J=7.7 Hz, CONH), 8.10 (1H, s, Ph-H)

Example C

Preparation of 4-amino-5-chloro-N-[1-(4-piperidinylmethyl)-4-piperidinyl]-2,3-dihydrobenzo[b]furan-7-carboxamide (1) Methyl 4-aceylamino-5-chloro-2,3-dihydrobenzo[b]furan-7-carboxylate (11.3 g), which is prepared by the method disclosed in Synlett, 1993, 269), is suspended in a mixture of methanol:water (1:1) (200 ml), and thereto is added dropwise a 2N aqueous sodium hydroxide solution (23 ml) under ice-cooling. The mixture is heated under reflux for 3 hours, and concentrated under reduced pressure to remove the methanol. To an aqueous solution of the residue is added a 2N aqueous hydrochloric acid solution, and the precipitated solid is collected by filtration, and dried to give 4-acetylamino-5-chloro-2,3-dihydrobenzo[b]furan-7-carboxylic acid (10.5 g).

(2) To a solution of the above product (4.6 g) in dimethylformamide (60 ml) is added N,N'-carbonyldiimidazole (2.9 g), and the mixture is stirred at room temperature for 30 minutes. To the mixture is further added dropwise a solution of 4-amino-1-(1-benzyloxycarbonyl-4-piperidinylmethyl)piperidine (6.0 g) in dimethylformamide (30 ml), and the mixture is stirred overnight at room temperature. The mixture is concentrated to dryness under reduced pressure, and the residue is dissolved in chloroform, washed successively with water and a saturated aqueous sodium chloride solution, and dried over anhydrous magnesium sulfate. The solvent is evaporated under reduced pressure to give crude 4-acetylamino-N-[1-(1-benzyloxycarbonyl-4-piperidinylmethyl)-4-piperidinyl]-5-chloro-2,3-dihydrobenzo [b]furan-7-carboxamide (11.3 g) as an oily product.

(3) To a solution of the above product (11.3 g) in methanol (52 ml) is added dropwise 1N aqueous sodium hydroxide solution (54 ml) under ice-cooling, and the mixture is heated under reflux for 5 hours. The reaction mixture is concentrated to dryness under reduced pressure, and the residue is dissolved in chloroform, washed successively with water and a saturated aqueous sodium chloride solution, and dried over anhydrous magnesium sulfate. The solvent is evaporated under reduced pressure to give crude 4-amino-N-[1-(1-benzyloxycarbonyl-4-piperidinylmethyl)-4-piperidinyl]-5-chloro-2,3-dihydrobenzo[b]furan-7 -carboxamide (7.59 g) as an oily product.

(4) The above product is treated in a similar manner as in Example B-(2) to give the desired compound.

$^{1}$H-NMR spectrum (CDCl$_3$, δ ppm): 0.95–1.20 (2H, m), 1.42–2.20 (12H, m), 2.50–2.65 (2H, m), 2.68–2.82 (2H, m), 3.00–3.12 (4H, m), 3.97 (1H, m), 4.26 (2H, brs, NH$_2$), 4.77 (2H, t, J=8.1 Hz), 7.25 (1H, d, J=7.8 Hz, CONH), 7.86 (1H, s, Ph-H)

Example D

Preparation of 4-amino-5-chloro-N-[1-(4-piperidinylmethyl)-4-piperidinyl]-2,2-dimethyl-2,3-dihydrobenzo[b]furan-7-carboxamide (1) Similar procedures as Example C-(2) are repeated except that 4-amino-5-chloro-2,2-dimethyl-2,3-dihydrobenzo[b]furan-7-carboxylic acid is used instead of 4-acetylamino-5-chloro-2,3-dihydrobenzo[b]-furan-7-carboxcylic acid in Example C-(2) to give 4-amino-5-chloro-N-[1-(1-benzyloxycarbonyl-4-piperidinylmethyl)-4-piperidinyl]-2,2-dimethyl-2,3-dihydrobenzo[b]furan-7-carboxamide.

(2) The above product is treated in a similar manner as in Example B-(2) to give the desired compound.

Example 1

Preparation of 4-amino-5-chloro-N-[1-(1-dimethylcarbamoyl-4-piperidinylmethyl)-4-piperidinyl]-2-methoxybenzamide To a solution of 4-amino-5-chloro-2-methoxy-N-[1-(4-piperidinylmethyl)-4-piperidinyl]benzamide (610 mg) in methylene chloride (30 ml) is added triethylamine (0.22 ml), and further thereto is added dimethylcarbamoyl chloride (0.15 ml) under ice-cooling. The mixture is stirred at room temperature for 5 hours. The reaction mixture is washed with water and a saturated aqueous sodium chloride solution, dried over anhydrous magnesium sulfate, and the solvent is evaporated under reduced pressure. The residue is purified by basic silica gel column chromatography (eluent; chloroform) to give the desired compound (720 mg) as white amorphous.

M.p. 124–126° C. (recrystallized from ethyl acetate-toluene)

The above obtained desired compound (free base) is dissolved in ethanol, and thereto is added fumaric acid, and the precipitated white crystals are collected by filtration, and dried to give the fumarate of the desired compound.

M.p. 223–225° C. (recrystallized from ethanol)

Examples 2–17

Using various carbamoyl chlorides, thiocarbamoyl chorides or sulfamoyl chlorides instead of dimethylcarbamoyl chloride in Example 1, the following compounds as listed in Table 3 are obtained in a similar manner as in Example 1.

TABLE 3

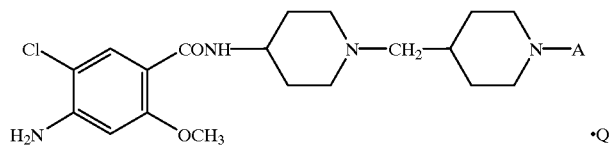

·Q

| Ex. No. | A | Q | M.p. (° C.) | Solv. for recrystal. |
|---|---|---|---|---|
| 2 | —CO—N(ET)$_2$ | Fumarate | 164–166 | E |
| 3 | —CO—N(iPr)$_2$ | ½ Fumarate, ½ EtOH | 192–194 | E |
| 4 | —CO—N(Me)Et | Fumarate, ¼ H$_2$O | 205–207 | E |
| 5 | —CO—N(Me)Pr | Fumarate, ¼ H$_2$O | 191–193 | E |
| 6 | —CO—N(Me)iPr | Fumarate, ¼ H$_2$O | 206–208 | E |
| 7 | —CO—N(Me)CH$_2$CH(Me)$_2$ | Fumarate, ¼ H$_2$O | 190–192 | E |
| 8 | —CO—N(Me)Ph | Fumarate | 171–173 | E |
| 9 | —CO—N(Ph)$_2$ | Fumarate, ¼ H$_2$O | 163–165 | E |
| 10 | —CS—N(Me)$_2$ | Fumarate | 212–214 | E |
| 10a | —CS—N(Me)$_2$ | — | 136–138 | MEK-T |
| 11 | —CS—N(Et)$_2$ | Fumarate, ½ H$_2$O | 171–173 | E |

TABLE 3-continued

Structure: 5-chloro-4-amino-2-methoxy-benzamide linked to N-[1-(4-piperidinylmethyl)-4-piperidinyl]-N-A · Q

| Ex. No. | A | Q | M.p. (° C.) | Solv. for recrystal. |
|---|---|---|---|---|
| 12 | —CO—N(pyrrolidine) | Fumarate | 223–225 | E |
| 12a | —CO—N(pyrrolidine) | ¼ H₂O | 156–158 | EA-T |
| 13 | —CO—N(morpholine) | Fumarate | 227–229 | E |
| 14 | —CO—N(thiomorpholine) | Fumarate, ¼ H₂O, ¼ EtOH | 236–238 | E |
| 15 | —CO—N(4-Me-piperazine) | 2 Fumarate, ¼ H₂O, ¼ EtOH | 204–206 | E |
| 16 | —SO₂N(Me)₂ | Fumarate | 215–217 | E |
| 17 | —CO—N(piperidine) | Fumarate | 225–227 | E |

Examples 18–23

The following compounds as listed in Table 4 are obtained in a similar manner as in Example 1 except that 4-amino-5-chloro-N-[1-(4-piperidinylmethyl)-4-piperidinyl]-2,3-dihydrobenzo[b]furan-7-carboxamide and the corresponding various carbamoyl chlorides or thiocarbamoyl chlorides are used instead of 4-amino-5-chloro-2-methoxy-N-[1-(4-piperidinylmethyl)-4-piperidinyl]benzamide and dimethyl-carbamoyl chloride in Example 1, respectively. However, the compounds of Examples 22 and 23 are obtained in a similar manner as in Example C-(2) by using the corresponding starting compounds.

TABLE 4

Structure: 5-chloro-4-amino-2,3-dihydrobenzo[b]furan-7-carboxamide linked to N-[1-(4-piperidinylmethyl)-4-piperidinyl]-N-A · Q

| Ex. No. | A | Q | M.p. (° C.) | Solv. for recrystal. |
|---|---|---|---|---|
| 18 | —CO—N(Me)₂ | Fumarate | 222–225 | E |
| 19 | —CO—N(Et)₂ | Fumarate | 172–174 | E |
| 20 | —CS—N(Me)₂ | ½ Fumarate, MeOH | 165–168 | M |
| 20a | —CS—N(Me)₂ | — | 179–180 | CF-EA |

TABLE 4-continued

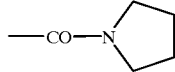

| Ex. No. | A | Q | M.p. (° C.) | Solv. for recrystal. |
|---|---|---|---|---|
| 21 | —CO—N(pyrrolidinyl) | Fumarate | 229–231 | M-E |
| 22 | —CO—NH₂ | ½ Fumarate | 205–207 | M-E |
| 23 | —CO—NH(Me) | Fumarate, ¼ H₂O | 212–214 | M-E |

Example 24

Preparation of 4-amino-5-chloro-N-[1-(1-dimethylthiocarbamoyl-4-piperidinylmethyl)-4-piperidinyl]-2,2-dimethyl-2,3-dihydrobenzo[b]-furan-7-carboxamide The desired compound is obtained in a similar manner as in Example 1 except that 4-amino-5-chloro-N-[1-(4-piperidinylmethyl)-4-piperidinyl]-2,2-dimethyl-2,3-dihydrobenzo[b]furan-7-carboxamide and dimethylthiocarbamoyl chloride are used instead of 4-amino-5-chloro-2-methoxy-N-[1-(4-piperidinylmethyl)-4-piperidinyl]benzamide and dimethylcarbamoyl chloride in Example 1, respectively.

The desired compound (free base) thus obtained is dissolved in ethanol, and thereto is added fumaric acid, and the precipitated crystals are collected by filtration, and dried to give the fumarate of the desired compound.

M.p. 193–195° C. (recrystallized from ethanol)

Example 25

Preparation of 4-amino-5-chloro-N-[1-(1-dimethylcarbamoyl-4-piperidinylmethyl)-4-piperidinyl]-2-ethoxybenzamide Similar procedures of Example C-(2) are repeated except that 4-amino-5-chloro-2-ethoxybenzoic acid and 4-amino-1-(1-dimethylcarbamoyl-4-piperidinylmethyl)piperidine are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2), respectively, and the obtained compound is recrystallized from ethanol to give the ½ ethanolate of the desired compound.

M.p. 207–209° C. (recrystallized from ethanol)

The desired compound (free base) thus obtained is dissolved in ethanol, and thereto is added fumaric acid, and the precipitated crystals are collected by filtration, and dried to give the fumarate ¼ hydrate of the desired compound.

M.p. 203–205° C. (recrystallized from ethanol)

Example 26

Preparation of 4-amino-5-bromo-N-[1-(1-dimethylcarbamoyl-4-piperidinylmethyl)-4-piperidinyl]-2-methoxybenzamide The desired compound is obtained in a similar manner as in Example C-(2) except that 4-amino-5-bromo-2-methoxybenzoic acid and 4-amino-1-(1-dimethylcarbamoyl-4-piperidinylmethyl)piperidine are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2), respectively.

The desired compound thus obtained is dissolved in ethanol, and thereto is added fumaric acid, and the precipitated crystals are collected by filtration, and dried to give the fumarate of the desired compound as white crystals.

M.p. 226–230° C. (recrystallized from ethanol)

Examples 27–36

The compounds as listed in Table 5 are obtained in a similar manner as in Example C-(2) except that the corresponding starting compounds are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2).

TABLE 5

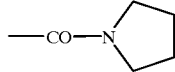

| Ex. No. | R⁴ | Q¹ | Q² | Q | M.p. (° C.) | Solv. for recrytal. |
|---|---|---|---|---|---|---|
| 27 | Et | Et | Et | ½ Fumarate, ½ H₂O, ½ EtOH | 154–157 | E |
| 27a | Et | Et | Et | — | 164–165 | E |
| 28 | Pr | Me | Me | Fumarate | 178–180 | E |
| 29 | Pr | Et | Et | Fumarate, EtOH | 115–118 | E |
| 30 | iPr | Me | Me | ½ Fumarate, ¼ H₂O, EtOH | 202–205 | E |
| 31 | iPr | Et | Et | Fumarate, EtOH | 114–117 | E |
| 32 | Et | —(CH₂)₄— | | Fumarate | 211–213 | E |

(Example 33)

4-Amino-5-chloro-N-[1-(1-dimethylthiocarbamoyl-4-piperidinylmethyl)-4-piperidinyl]-2-ethoxybenzamide.fumarate.½ hydrate: m.p. 210–212° C. (recrystallized from ethanol)

(Example 34)

4-Amino-5-bromo-2-methoxy-N-[1-[1(1-pyrrolidinecarbonyl)-4-piperidinylmethyl]-4-piperidinyl]benzamide fumarate: m.p. 221–225° C. (recrystallized from ethanol)

(Example 35)

4-Amino-5-bromo-N-[1-(1-carbamoyl-4-piperidinylmethyl)-4-piperidinyl]-2-methoxybenzamide.½ fumarate.¼ ethanolate: m.p. 228–230° C. (recrystallized from ethanol)

(Example 36)

4-Amino-5-bromo-2-methoxy-N-[1-(1-methylcarbamoyl-4-piperidinylmethyl)-4-piperidinyl]benzamide fumarate: m.p. 206–208° C. (recrystallized from ethanol)

Example 37

Preparation of 4-amino-5-chloro-2-methoxy-N-[1-(1-phenylcarbamoyl-4-piperidinylmethyl)-4-piperidinyl]benzamide To a solution of chloromethyl N-phenylcarbamate (220 mg), which is prepared by the method disclosed in Synth. Commun., 1996, 26, 4253, in ethanol (20 ml) is added dropwise a solution of 4-amino-5-chloro-2-methoxy-N-[1-(4-piperidinylmethyl)-4-piperidinyl]benzamide (910 mg) in ethanol (10 ml) at room temperature, and the mixture is stirred at room temperature for 7 hours. The mixture is concentrated to dryness under reduced pressure, and the residue is dissolved in chloroform, washed with water and a saturated aqueous sodium chloride solution, dried over anhydrous magnesium sulfate, and the solvent is evaporated under reduced pressure. The residue is purified by silica gel column chromatography (eluent; chloroform:methanol= 30:1) to give the desired compound (480 mg) as white amorphous.

The desired compound (free base) (470 mg) thus obtained is dissolved in ethanol, and thereto is added fumaric acid (110 mg), and the precipitated white crystals are collected by filtration, and dried to give the fumarate.¼ hydrate (530 mg) of the desired compound.

M.p. 212–214° C. (recrystallized from ethanol)

Examples 38–51

The compounds as listed in Table 6 are obtained in a similar manner as in Example 37 except that the corresponding chloromethyl N-substituted carbamates are used instead of chloromethyl N-phenylcarbamate in Example 37.

TALBE 6

| Ex. No. | $Q^2$ | Q | M.p. (° C.) | Solv. for recrystal. |
|---|---|---|---|---|
| 38 | Ph-4-Cl* | Fumarate, ¼ H$_2$O | 213–215 | E |
| 39 | Ph-4-OMe | Fumarate, ¾ H$_2$O | 188–190 | M-E |
| 40 | Ph-4-Me | Fumarate, ½ H$_2$O | 197–199 | E |
| 41 | Ph-4-COOEt | Fumarate, ¼ H$_2$O | 214–216 | E |
| 42 | Pr | Fumarate | 215–217 | E |
| 43 | iPr | Fumarate | 209–211 | E |

TALBE 6-continued

| Ex. No. | $Q^2$ | Q | M.p. (° C.) | Solv. for recrystal. |
|---|---|---|---|---|
| 44 | Bu | Fumarate | 211–213 | E |
| 45 | iBu | Fumarate | 220–222 | E |
| 46 | tBu | Fumarate | 203–205 | E |
| 47 | CH$_2$Ph | Fumarate, ¼ H$_2$O | 197–199 | E |
| 48 | Cyclopropyl | Fumarate | 213–215 | E |
| 49 | Cyclopentyl | Fumarate | 214–216 | E |
| 50 | Cyclohexyl | Fumarate | 211–213 | E |
| 51 | Cycloheptyl | Fumarate | 193–195 | E |

*Ph-4-Cl means 4-chlorophenyl group.

Example 52

Preparation of 4-amino-5-chloro-N-[1-(1-phenylcarbamoyl-4-piperidinylmethyl)-4-piperidinyl]-2,3-dihydrobenzo[b]furan-7-carboxamide The fumarate of the desired compound is obtained in a similar manner as in Example 37 except that 4-amino-5-chloro-N-[1-(4-piperidinylmethyl)-4-piperidinyl]-2,3-dihydrobenzo[b]furan-7-carboxamide is used instead of 4-amino-5-chloro-2-methoxy-N-[1-(4-piperidinylmethyl)-4-piperidinyl]benzamide in Example 37.

M.p. 213–215° C. (recrystallized from ethanol)

Example 53

Preparation of 4-amino-N-[1-(1-carbamoyl-4-piperidinylmethyl)-4-piperidinyl]-5-chloro-2-methoxybenzamide To a solution of 4-amino-5-chloro-2-methoxy-N-[1-(4-piperidinylmethyl)-4-piperidinyl]benzamide (610 mg) in methylene chloride (30 ml) is added trimethylsilyl isocyanate (180 mg) under ice-cooling, and the mixture is stirred at room temperature for 15 hours. The reaction mixture is washed with water and a saturated aqueous sodium chloride solution, dried over anhydrous magnesium sulfate, and the solvent is evaporated under reduced pressure. The residue is purified by basic silica gel column chromatography (eluent; chloroform: methanol=40:1) to give 4-amino-5-chloro-N-[1-(1-carbamoyl-4-piperidinylmethyl)-4-piperidinyl]-2-methoxybenzamide (440 mg) as white amorphous.

The desired compound (free base) thus obtained is dissolved in ethanol, and thereto is added fumaric acid, and the precipitated white crystals are collected by filtration, and dried to give the ½ fumarate. ½ ethanolate of the desired compound.

M.p. 222–224° C. (recrystallized from ethanol)

Example 54

Preparation of 4-amino-5-chloro-N-[1-(1-ethylcarbamoyl-4-piperidinylmethyl)-4-piperidinyl]-2-methoxybenzamide The fumarate of the desired compound is obtained in a similar manner as in Example 53 except that ethyl isocyanate is used instead of trimethylsilyl isocyanate in Example 53.

M.p. 215–217° C. (recrystallized from ethanol)

Example 55

Preparation of 4-amino-5-chloro-2-methoxy-N-[1-[1-(1-pyrrolidinecarbonyl)-4-piperidinylmethyl]-4-piperidinyl]benzamide (the same of the compound of Example 12)

To 4-amino-5-chloro-2-methoxy-N-[1-(1-phenoxycarbonyl-4-piperidinylmethyl)-4-piperidinyl]benzamide (1 g), which is prepared in the same manner as in Example 1 except that phenyl chloroformate is used instead of dimethylcarbamoyl chloride, is added pyrrolidine (3 ml), and the mixture is heated under reflux for 10 hours. The mixture is concentrated to dryness under reduced pressure, and to the residue is added chloroform. The solution is washed with water and a saturated aqueous sodium chloride solution, dried over anhydrous magnesium sulfate, and the solvent is evaporated under reduced pressure. The residue is purified by silica gel column chromatography (eluent; chloroform:methanol=40:1) to give the desired compound (790 mg) as white amorphous.

The desired compound (free base) thus obtained is dissolved in ethanol, and thereto is added fumaric acid, and the precipitated white crystals are collected by filtration, and dried to give the fumarate of the desired compound as white crystals.

M.p. 223–225° C. (recrystallized from ethanol)

Example 56

Preparation of 4-amino-5-chloro-2-methoxy-N-[1-(1-methylcarbamoyl-4-piperidinylmethyl)-4-piperidinyl]benzamide To 4-amino-5-chloro-2-methoxy-N-[1-(1-phenoxycarbonyl-4-piperidinylmethyl)-4-piperidinyl]benzamide (880 mg), which is prepared in a similar manner as in Example 1 except that phenyl chloroformate is used instead of dimethylcarbamoyl chloride, is added a 30% solution of methylamine in ethanol (20 ml), and the mixture is heated at 110° C. for 8 hours in a sealed tube. The mixture is concentrated to dryness under reduced pressure, and to the residue is added chloroform. The solution is washed with water and a saturated aqueous sodium chloride solution, dried over anhydrous magnesium sulfate, and concentrated under reduced pressure. The residue is purified by silica gel column chromatography (eluent; chloroform:methanol=20:110:1) to give the desired compound (200 mg) as amorphous.

The desired compound thus obtained is dissolved in ethanol, and thereto is added fumaric acid, and the precipitated crystals are collected by filtration, and dried to give the fumarate.½ hydrate of the desired compound.

M.p. 202–204° C. (recrystallized from ethanol)

Example 57

Preparation of 4-amino-5-chloro-2-hydroxy-N-[1-[1-(1-piperidinecarbonyl)-4-piperidinylmethyl]4-piperidinyl]benzamide The fumarate of the desired compound is obtained in a similar manner as in Example 55 except that piperidine is used instead of pyrrolidine in Example 55.

M.p. 210–212° C. (recrystallized from ethanol)

Example 58

Preparation of 4-amino-5-chloro-N-[1-(1-dimethylcarbamoyl-4-piperidinylmethyl)-4-piperidinyl]-2-hydroxybenzamide The fumarate of the desired compound is obtained in a similar manner as in Example C-(2) except that 4-amino-5-chloro-2-hydroxybenzoic acid and 4-amino-1-(1-dimethylcarbamoyl-4-piperidinylmethyl)-piperidine are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2), respectively.

M.p. 211–213° C. (recrystallized from ethanol)

Example 59

Preparation of 4-amino-5-chloro-2-hydroxy-N-[1-[1-(1-pyrrolidinecarbonyl)-4-piperidinylmethyl]-4-piperidinyl]benzamide The fumarate.¼ hydrate of the desired compound is obtained in a similar manner as in Example C-(2) except that 4-amino-5-chloro-2-hydroxybenzoic acid and 4-amino-1-[1-(1-pyrrolidinecarbonyl)-4-piperidinylmethyl]piperidine are used instead of 4-acetylamino-5-chloro-2,3-dihydrobenzo[b]furan-7-carboxylic acid and 4-amino-1-(1-benzyloxycarbonyl-4-piperidinylmethyl) piperidine in Example C-(2), respectively.

M.p. 209–21 1° C. (recrystallized from ethanol-isopropanol)

Example 60

Preparation of 4-amino-5-chloro-2-methoxy-N-1-[1-(4-methoxybenzoyl)-4-piperidinylmethyl]-4-piperidinyl]benzamide To a solution of 4-amino-5-chloro-2-methoxy-N-[1-(4-piperidinylmethyl)-4-piperidinyl]benzamide (610 mg), 4-methoxybenzoic acid (220 mg), and benzotriazol-1-yloxytris(dimethylamino)-phosphonium.hexafluorophosphate (BOP reagent) (710 mg) in methylene chloride (30 ml) is added triethylamine (0.33 ml) at room temperature, and the mixture is stirred for 5 hours. The reaction mixture is washed with water, a saturated aqueous sodium hydrogen carbonate solution, and a saturated aqueous sodium chloride solution, dried over anhydrous sodium sulfate, and the solvent is evaporated under reduced pressure. The residue is purified by silica gel column chromatography (eluent; chloroform:methanol= 40:1→20:1) to give the desired compound (650 mg) as yellow amorphous.

The desired compound (free base) thus obtained is dissolved in ethanol, and thereto is added a solution of fumaric acid in ethanol, and the precipitated white crystals are collected by filtration, and dried to give the fumarate.monohydrate of the desired compound.

M.p. 187–189° C. (recrystallized from ethanol)

Examples 61–71

The compounds as listed in Table 7 are obtained in a similar manner as in Example 60 except that the various carboxylic acids are used instead of 4-methoxycarboxylic acid in Example 60.

TABLE 7

Cl—[benzene]—CONH—[piperidine]—N—CH$_2$—[piperidine]—N—CO—R$^7$
H$_2$N—   —OCH$_3$   · Q

| Ex. No. | R$^7$ | Q | M.p. (° C.) | Solv. for recrystal. |
|---|---|---|---|---|
| 61 | Ph-4-Me* | Fumarate | 207–209 | E |
| 62 | Ph-2-OMe-4-NH$_2$-5-Cl | ¼ H$_2$O | 259–261 | M-E |
| 63 | —CH$_2$OMe | Fumarate | 209–211 | E |
| 64 | —(CH$_2$)$_2$—OMe | Fumarate | 184–186 | E |
| 65 | —(CH$_2$)$_2$—OH | Fumarate | 213–215 | E |
| 66 | —(CH$_2$)$_2$—OEt | Fumarate | 194–196 | E |
| 67 | —(CH$_2$)$_3$—OEt | Fumarate | 190–192 | E |
| 68 | —(CH$_2$)$_3$—OPr | Fumarate | 182–184 | E |
| 69 | —(CH$_2$)$_3$—COOMe | Fumarate | 201–203 | E |
| 70 | Et | Fumarate | 230–232 | E |
| 71 | Pr | Fumarate | 222–224 | E |

*Ph-4-Me means 4-methylphenyl group.

Example 72

Preparation of 4-amino-N-[1-(1-benzoyl-4-piperidinylmethyl)-4-piperidinyl]-5-chloro-2-methoxybenzamide To a solution of 4-amino-5-chloro-2-methoxy-N-[1-(4-piperidinylmethyl)-4-piperidinyl]benzamide (610 mg) and triethylamine (0.22 ml) in methylene chloride (30 ml) is added benzoyl chloride (0.19 ml) at room temperature, and the mixture is stirred for 5 hours. The reaction mixture is washed with water, and a saturated aqueous sodium chloride solution, dried over anhydrous magnesium sulfate, and the solvent is evaporated under reduced pressure. The residue is purified by silica gel column chromatography (eluent; chloroform: methanol=20:1) to give the desired compound (610 mg).

M.p. 114–116° C. (recrystallized from ethanol)

Examples 73–78

The compounds as listed in Table 8 are obtained in a similar manner as in Example 72 except that various acid chlorides or alkyl chloroformates are used instead of benzoyl chloride in Example 72.

TABLE 8

Cl—[benzene]—CONH—[piperidine]—N—CH$_2$—[piperidine]—N—CO—R$^7$
H$_2$N—   —OCH$_3$   · Q

| Ex. No. | R$^7$ | Q | M.p. (° C.) | Solv. for recrystal. |
|---|---|---|---|---|
| 73 | Ph-4-Cl | Fumarate, ¼ H$_2$O | 222–224 | E |
| 74 | Ph-3,4,5-(OMe)$_3$* | ¼ H$_2$O | 198–200 | M-E |
| 75 | Me | Fumarate | 229–231 | E |
| 76 | —OMe | Fumarate, ½ H$_2$O | 233–235 | E |
| 77 | —OEt | Fumarate | 220–222 | M-E |
| 78 | —COOEt | Fumarate | 203–205 | E |

*Ph-3,4,5-(OMe)$_3$ means 3,4,5-trimethoxyphenyl group.

Example 79

Preparation of 4-amino-5-chloro-N-[1-(1-formyl-4-piperidinylmethyl)-4-piperidinyl]-2-methoxybenzamide To a solution of imidazole (330 mg) in dimethylformamide (0.74 ml) is added trimethylsilyl chloride (0.61 ml) at room temperature, and the mixture is stirred for 20 minutes. To the solution is added 4-amino-5-chloro-2-methoxy-N-[1-(4-piperidinylmethyl)-4-piperidinyl]-benzamide (610 mg), and the mixture is stirred at room temperature for 24 hours. To the reaction mixture is added a small amount of water, and the mixture is concentrated to dryness under reduced pressure. To the residue is added water, and the mixture is extracted with chloroform. The organic layer is washed with a saturated aqueous sodium chloride solution, dried over anhydrous sodium sulfate, and the solvent is evaporated under reduced pressure. The residue is purified by silica gel column chromatography (eluent; chloroform:methanol=30:1→20:1) to give the desired compound (200 mg) as amorphous.

The desired compound (free base) thus obtained is dissolved in ethanol, and thereto is added a solution of fumaric acid in ethanol, and the precipitated crystals are collected by filtration, and dried to give the fumarate of the desired compound as white crystals.

M.p. 206–208° C. (recrystallized from ethanol)

Example 80

Preparation of 4-amino-5-chloro-2-methoxy-N-[1-[1-(4-methoxybutyryl)-4-piperidinylmethyl]-4-piperidinyl]benzamide The desired compound is obtained in a similar manner as in Example 60 except that 4-methoxybutyric acid, which is prepared by the method disclosed in J. Org. Chem. 1994, 59, 2253, is used instead of 4-methoxybenzoic acid in Example 60.

The desired compound (free base) thus obtained is dissolved in ethanol, and thereto is added a solution of fumaric acid in ethanol, and the precipitated crystals are collected by filtration, and dried to give the fumarate of the desired compound.

M.p. 200–202° C. (recrystallized from ethanol)

Example 81

Preparation of 4-amino-5-chloro-2-ethoxy-N-[1-[1-(3-methoxypropionyl)-4-piperidinylmethyl]-4-piperidinyl]benzamide The desired compound is obtained in a similar manner as in Example C-(2) except that 4-amino-5-chloro-2-ethoxybenzoic acid and 4-amino-1-[1-(3-methoxypropionyl)-4-piperidinylmethyl]piperidine are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2), respectively.

The desired compound (free base) thus obtained is dissolved in ethanol, and thereto is added a solution of fumaric acid in ethanol, and the precipitated crystals are collected by filtration, and dried to give the fumarate.½ ethanolate of the desired compound.

M.p. 175–177° C. (recrystallized from ethanol)

Example 82

Preparation of 4-amino-5-bromo-2-methoxy-N-[1-[1-(3-methoxypropionyl)-4-piperidinylmethyl]-4-piperidinyl]benzamide The desired compound is obtained in a similar manner as in Example 81 except that 4-amino-5-bromo-2- methoxybenzoic acid is used instead of 4-amino-5-chloro-2-ethoxybenzoic acid in Example 81.

The desired compound (free base) thus obtained is dissolved in ethanol, and thereto is added a solution of fumaric acid in ethanol, and the precipitated crystals are collected by filtration, and dried to give the fumarate of the desired compound.

M.p. 207–209° C. (recrystallized from ethanol)

Example 83

Preparation of 4-amino-5-bromo-2-methoxy-N-[1-(1-methoxycarbonyl-4-piperidinylmethyl)-4-piperidinyl]benzamide The desired compound is obtained in the same manner as in Example C-(2) except that 4-amino-5-bromo-2-methoxybenzoic acid and 4-amino-1-(1-methoxycarbonyl-4-piperidinylmethyl]piperidine are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2), respectively.

The desired compound (free base) thus obtained is dissolved in ethanol, and thereto is added a solution of fumaric acid in ethanol, and the precipitated crystals are collected by filtration, and dried to give the fumarate of the desired compound.

M.p. 233–235° C. (recrystallized from ethanol)

Example 84

Preparation of 4-amino-N-[1-[1-(2-butanon-3-yl)-4-piperidinylmethyl]-4-piperidinyl]-5-chloro-2-methoxybenzamide To a solution of 4-amino-5-chloro-2-methoxy-N-[1-(4-piperidinylmethyl)-4-piperidinyl]benzamide (610 mg) in acetonitrile (30 ml) are added potassium carbonate (80 mg) and 3-chloro-2-butanone (220 mg), and the mixture is heated under reflux for 16 hours, and concentrated to dryness under reduced pressure. The residue is dissolved in chloroform, and the mixture is washed with water and a saturated aqueous sodium chloride solution, dried over anhydrous magnesium sulfate, and the solvent is evaporated under reduced pressure. The residue is purified by silica gel column chromatography (eluent; chloroform:methanol= 15:1) to give the desired compound (640 mg) as a yellow oily product.

The desired compound (free base) thus obtained is dissolved in ethanol, and thereto is added a solution of fumaric acid in methanol, and the precipitated crystals are collected by filtration, and dried to give the difumarate.¼ hydrate of the desired compound as white crystals.

M.p. 268–270° C. (recrystallized from methanol-ethanol)

Examples 85–98

The compounds as listed in Table 9 are obtained in a similar manner as in Example 84 except that various alkyl halide derivatives are used instead of 3-chloro-2-butanone in Example 84.

TABLE 9

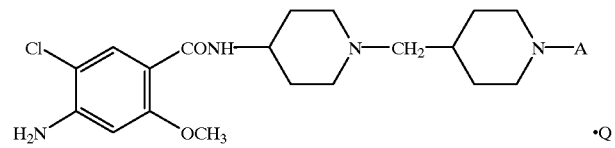

·Q

| Ex. No. | A | Q | M.p. (° C.) | Solv. for recrystal. |
|---|---|---|---|---|
| 85 | —CH$_2$COMe | ½ Fumarate, ¾ EtOH | 202–204 | M-E |
| 86 | —CH$_2$COEt | ½ Fumarate, ¼ EtOH | 185–187 | E |
| 86a | —CH$_2$COE5 | ¾ H$_2$O | 97–100 | EA-HX |
| 87 | —CH$_2$COC(Me)$_3$ | 2 Fumarate | 202–204 | E |
| 88 | —(CH$_2$)$_3$—COMe | 2 Fumarate, ¼ H$_2$O | 163–165 | E |
| 89 | —(CH$_2$)$_2$—COEt | 2 Fumarate | 195–197 | E |
| 90 | —CH$_2$COOEt | Fumarate | 193–195 | E |
| 91 | —(CH$_2$)$_2$—COOEt | 2 Fumarate | 203–205 | E |
| 92 | —(CH$_2$)$_3$—COOEt | 2 Fumarate | 177–180 | M-E |
| 93 | —(CH$_2$)$_4$—COOEt | 2 Fumarate | 184–186 | E |
| 94 | —(CH$_2$)$_5$—COOEt | 2 Fumarate, ¼ H$_2$O | 177–179 | E |
| 95 | —(CH$_2$)$_2$—CH(Me)COOMe | 2 Fumarate | 191–193 | M-E |
| 96 | —CH(Me)COOEt | ½ Fumarate | 199–201 | E |
| 97 | —CH(Et)—COOEt | ½ Fumarate, ½ H$_2$O | 190–192 | E |
| 98 | —CH(Bu)COOEt | ½ Fumarate | 200–202 | E |

Example 99

Preparation of 4-amino-N-[1-[1-(2-butanon-1-yl)-4-piperidinylmethyl]-4-piperidinyl]-5-chloro-2,3-dihydrobenzo[b]furan-7-carboxamide The difumarate.¼ hydrate.½ ethanolate of the desired compound is obtained in a similar manner as in Example 84 except that 4-amino-5-chloro-N-[1-(4-piperidinylmethyl)-4-piperidinyl]-2,3-dihydrobenzo[b]furan-7-carboxamide and 1-chloro-2-butanone are used instead of 4-amino-5-chloro-2-methoxy-N-[1-(4-piperidinylmethyl)-4-piperidinyl]benzamide and 3-chloro-2-butanone in Example 84, respectively.

M.p. 210–213° C. (recrystallized from ethanol)

Example 100

Preparation of 4-amino-5-chloro-N-[1-[1-(3-ethoxycarbonylpropyl)-4-piperidinylmethyl]-4-piperidinyl]-2,3-dihydrobenzo[b]furan-7-carboxamide The difumarate of the desired compound is obtained in a similar manner as in Example 84 except that 4-amino-5-chloro-N-[1-(4-piperidinylmethyl)-4-piperidinyl]-2,3-dihydrobenzo[b]furan-7-carboxamide and ethyl 4-chlorobutyrate are used instead of 4-amino-5-chloro-2-methoxy-N-[1-(4-piperidinylmethyl)-4-piperidinyl]benzamide and 3-chloro-2-butanone in Example 84, respectively.

M.p. 188–189° C. (recrystallized from ethanol)

Examples 101–105

The following compounds are obtained in a similar manner as in Example C-(2) except that the corresponding starting compounds are used instead of 4-acetylamino-5-chloro-2,3-dihydrobenzo[b]furan-7-carboxylic acid and 4-amino-1-(1-benzyloxycarbonyl-4-piperidinylmethyl)piperidine in Example C-(2).

(Example 101)
4-Amino-N-[1-(1-dimethylcarbamoyl-4-piperidinylmethyl)-4-piperidinyl]-5-iodo-2-methoxybenzamide fumarate: m.p. 232–234° C. (recrystallized from methanol-ethanol)

(Example 102)
4-Amino-5-iodo-2-methoxy-N-[1-[1-(1-pyrrolidinecarbonyl)-4-piperidinylmethyl]-4-piperidinyl]benzamide.fumarate: m.p. 235–237° C. (recrystallized from methanol-ethanol)

(Example 103)
4-Amino-5-chloro-N-[1-[1-(1-morpholinecarbonyl)-4-piperidinylmethyl]-4-piperidinyl]-2,3-dihydrobenzo[b]furan-7-carboxamide fumarate.¼ethanolate: m.p. 230–232° C. (recrystallized from ethanol)

(Example 104)
N-[1-(1-Acetyl-4-piperidinylmethyl)-4-piperidinyl]-4-amino-5-chloro-2,3-dihydrobenzo[b]furan-7-carboxamide fumarate: m.p. 235–237° C. (recrystallized from ethanol)

(Example 105)
4-Amino-5-chloro-N-[1-(1-dimethylsulfamoyl-4-piperidinylmethyl)-4-piperidinyl]-2,3-dihydrobenzo[b]furan-7-carboxamide fumarate: m.p. 236–238° C. (recrystallized from ethanol)

Example 106

Preparation of 4-amino-5-chloro-N-[1-[1-(1-hexahydroazepinecarbonyl)-4-piperidinylmethyl]-4-piperidinyl]-2-methoxybenzamide The fumarate of the desired compound is obtained in a similar manner as in Example 1 except that hexahydroazepinecarbonyl chloride, which is prepared by a conventional method, is used instead of dimethylcarbamoyl chloride in Example 1.

M.p. 213–215° C. (recrystallized from ethanol)

Preparation 1: Preparation of Tablets:

| | |
|---|---|
| 4-Amino-5-chloro-N-[1-(1-dimethylcarbamoyl-4-piperidinylmethyl)-4-piperidinyl]-2-methoxybenzamide fumarate | 5 g |
| Lactose | 80 g |
| Corn starch | 30 g |
| Crystalline cellulose | 25 g |
| Hydroxypropyl cellulose | 3 g |
| Light anhydrous silicic acid | 0.7 g |
| Magnesium stearate | 1.3 g |

The above components are mixed and kneaded in a conventional manner, and the mixture is granulated. The mixture is further tabletted to give 1,000 tablets (each 145 mg).

Preparation 2: Preparation of Capsules

| | |
|---|---|
| 4-Amino-5-chloro-N-[1-(1-dimethylcarbamoyl-4-piperidinylmethyl)-4-piperidinyl]-2-methoxybenzamide fumarate | 10 g |
| Lactose | 160 g |
| Corn starch | 22 g |
| Hydroxypropyl cellulose | 3.5 g |
| Light anhydrous silicic acid | 1.8 g |
| Magnesium stearate | 2.7 g |

The above components are mixed and kneaded in a conventional manner, and the mixture is granulated, and each 200 mg of the resultant is packed into a capsule to give 1,000 capsules.

| | |
|---|---|
| 4-Amino-5-chloro-N-[1-(1-dimethylcarbamoyl-4-piperidinylmethyl)-4-piperidinyl]-2-methoxybenzamide fumarate | 10 g |
| Lactose | 960 g |
| Hydroxypropyl cellulose | 25 g |
| Light anhydrous silicic acid | 5 g |

The above components are mixed by a conventional manner to give a powder preparation.

Preparation 4: Preparation of Injection (amount for 1000 ampoules)

| | |
|---|---|
| 4-Amino-5-chloro-N-[1-(1-dimethylcarbamoyl-4-piperidinylmethyl)-4-piperidinyl]2-methoxybenzamide fumarate | 10 g |
| Sorbitol | 100 g |
| Distilled water for injection | q.s. |
| Totally | 2000 ml |

4-Amino-5-chloro-N-[1-(1-dimethylcarbamoyl-4-piperidinylmethyl)-4-piperidinyl]-2-methoxybenzamide fumarate and sorbitol are dissolved in a portion of distilled water for injection, and thereto is added a remaining portion of distilled water for injection to adjust the total volume of the mixture. The solution thus obtained is filtered through a membrane filter (0.22 μm), and each 2 ml of the filtrate is filled into ampoules, which are further sterilized at 121° C. for 20 minutes.

INDUSTRIAL APPLICABILITY

The compound (I) of the present invention and a pharmaceutically acceptable acid addition salt thereof show a potent affinity for 5-HT$_4$ receptors, and can be useful in the prophylaxis or treatment of various diseases such as gastrointestinal diseases (e.g., irritable bowel syndrome, flaccid constipation, habitual constipation, drug-induced constipation (e.g., constipation induced by morphine, a psychotropic), chronic diarrhea, etc.), central nervous diseases (e.g., schizophrenia, depression, disturbance of memory, anxiety, etc.), urinary diseases such as dysuria accompanied by urinary obstruction or prostatomegaly, or various gastrointestinal function disorders (e.g., anorexia, nausea, vomiting, abdominal fullness, etc.) accompanied by the treatment of various diseases. Therefore, they are useful especially as a gastrointestinal motility enhancer or a gastrointestinal prokinetic agent.

What is claimed is:

1. A compound of the formula (I):

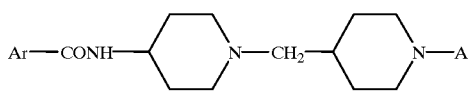
(I)

wherein Ar is a group of the following formula (Ar-1) or (Ar-2):

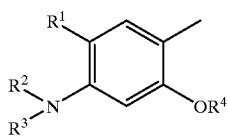
(Ar-1)

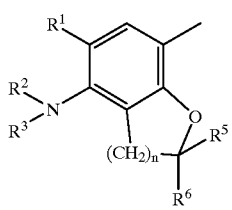
(Ar-2)

(in which $R^1$ is a halogen atom,
$R^2$ is a hydrogen atom or a lower alkyl group,
$R^3$ is a hydrogen atom, a lower alkyl group, or a lower alkanoyl group,
$R^4$ is a hydrogen atom or a lower alkyl group, and
$R^5$ and $R^6$ are the same or different and each a hydrogen atom or a lower alkyl group, and
n is 1, 2 or 3), A is a group of the following formula (A-1), (A-2) or (A-3):

—Z—N($Q^1$)($Q^2$)   (A-1)

(in which Z is —CO—, —CS— or —SO$_2$—,
$Q^1$ and $Q^2$ are the same or different and each a hydrogen atom, a lower alkyl group, a cycloalkyl group, a substituted or unsubstituted phenyl group, or a substituted or unsubstituted phenyl-lower alkyl group, or $Q^1$ and $Q^2$ may combine together with the nitrogen atom to which they bond to form a pyrrolidine ring, a piperidine ring, a hexahydroazepine ring, a morpholine ring, a thiomorpholine ring, or a piperazine ring having optionally a lower alkyl or benzyl substituent on the other nitrogen atom);

—CO—$R^7$   (A-2)

(in which $R^7$ is a hydrogen atom, a lower alkyl group, a lower alkoxy group, a lower alkoxycarbonyl group, a lower alkyl group being substituted by a hydroxy, lower alkoxy or lower alkoxycarbonyl group, or a substituted or unsubstituted phenyl group);

—(CH$_2$)$_p$—CH($R^8$)—COR$^9$   (A-3)

(in which p is 0, 1, 2, 3, 4 or 5,
$R^8$ is a hydrogen atom or a lower alkyl group, and
$R^9$ is a lower alkyl group or a lower alkoxy group), or a pharmaceutically acceptable acid addition salt thereof.

2. The compound according to claim 1, wherein in the formula (Ar-1), $R^2$ and $R^3$ are both hydrogen atoms and $R^4$ is a methyl group, an ethyl group, a propyl group or an isopropyl group, or in the formula (Ar-2), $R^2$ and $R^3$ are both hydrogen atoms, $R^5$ and $R^6$ are both hydrogen atoms or one of them is a methyl group, and the other is a hydrogen atom, and n is 1, or a pharmaceutically acceptable acid addition salt thereof.

3. A compound of the formula (I-1):

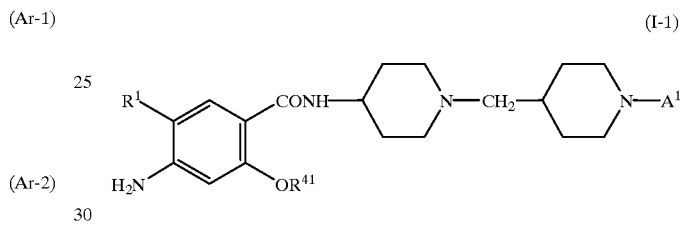
(I-1)

wherein $R^1$ is a halogen atom, $R^{41}$ is a methyl group, an ethyl group, a propyl group, or an isopropyl group, $A^1$ is a group of the following formula ($A^1$-1), ($A^1$-2) or ($A^1$-3):

—Z—N($Q^{11}$)($Q^{21}$)   ($A^1$-1)

(in which Z is —CO—, —CS— or —SO$_2$—, $Q^1$ and $Q^{21}$ are the same or different and each a methyl group, an ethyl group, a propyl group, or an isopropyl group, or $Q^{11}$ is a hydrogen atom, and $Q^{21}$ is a cyclopentyl group, a cyclohexyl group, a cycloheptyl group, or a substituted or unsubstituted phenyl group (said substituents may be a halogen atom, a C$_1$–C$_4$ alkyl group or a C$_1$–C$_4$ alkoxy group), or $Q^{11}$ and $Q^{21}$ may combine together with the nitrogen atom to which they bond to form a pyrrolidine ring or a morpholine ring);

—CO—$R^{71}$   ($A^1$-2)

(in which $R^{71}$ is a hydrogen atom, a methyl, an ethyl group, a propyl group, a methoxy group, an ethoxy group, a C$_1$–C$_4$ alkyl group being substituted by a methoxy, ethoxy, methoxycarbonyl or ethoxycarbonyl group, or a substituted or unsubstituted phenyl group (said substituents may be 1 to 3 groups selected from a halogen atom, a C$_1$–C$_4$ alkyl group, a C$_1$–C$_4$ alkoxy group and an amino group);

—(CH$_2$)p'—CH($R^{81}$)—COR$^{91}$   ($A^1$-3)

(in which p' is 0, 1 or 2, $R^{81}$ is a hydrogen atom, a methyl group, or an ethyl group, $R^{91}$ is a methyl group, an ethyl group, a methoxy group, or an ethoxy group), or a pharmaceutically acceptable acid addition salt thereof.

4. A compound of the (I-1'):

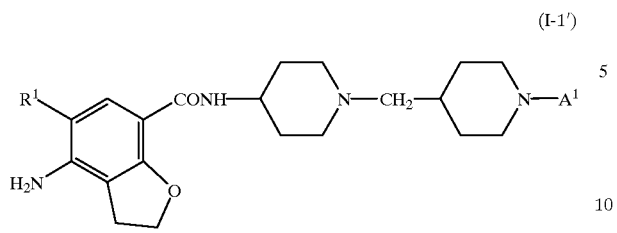

(I-1')

wherein $R^1$ is a halogen atom, and $A^1$ is a group of the following formula ($A^1$-1), ($A^1$-2) or ($A^1$-3):

$$—Z—N(Q^{11})(Q^{21}) \quad (A^1\text{-}1)$$

(in which Z is —CO—, —CS— or —SO$_2$—, $Q^{11}$ and $Q^{21}$ are the same or different and each a methyl group, an ethyl group, a propyl group, or an isopropyl group, or $Q^{11}$ is a hydrogen atom, and $Q^{21}$ is a cyclopentyl group, a cyclohexyl group, a cycloheptyl group, or a substituted or unsubstituted phenyl group (said substituents may be a halogen atom, a $C_1$–$C_4$ alkyl group or a $C_1$–$C_4$ alkoxy group), or $Q^{11}$ and $Q^{21}$ may combine together with the nitrogen atom to which they bond to form a pyrrolidine ring or a morpholine ring);

$$—CO—R^{71} \quad (A^1\text{-}2)$$

(in which $R^{71}$ is a hydrogen atom, a methyl, an ethyl group, a propyl group, a methoxy group, an ethoxy group, a $C_1$–$C_4$ alkyl group being substituted by a methoxy, ethoxy, methoxycarbonyl or ethoxycarbonyl group, or a substituted or unsubstituted phenyl group (said substituents may be 1 to 3 groups selected from a halogen atom, a $C_1$–$C_4$ alkyl group, a $C_1$–$C_4$ alkoxy group and an amino group);

$$—(CH_2)p'—CH(R^{81})—COR^{91} \quad (A^1\text{-}3)$$

(in which p' is 0, 1 or 2, $R^{81}$ is a hydrogen atom, a methyl group, or an ethyl group, $R^{91}$ is a methyl group, an ethyl group, a methoxy group, or an ethoxy group), or a pharmaceutically acceptable acid addition salt thereof.

5. A compound of the formula (I-2):

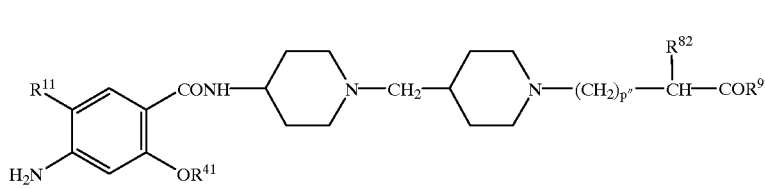

(I-2)

wherein $R^{11}$ is a chlorine atom or a bromine atom, $R^{41}$ is a methyl group, an ethyl group, a propyl group, or an isopropyl group, $R^{82}$ is a hydrogen atom, a methyl group, or an ethyl group, $R^{92}$ is a methyl group, an ethyl group, or an ethoxy group, and p" is 0, 1 or 2, or a pharmaceutically acceptable acid addition salt thereof.

6. A compound of the formula (I-3):

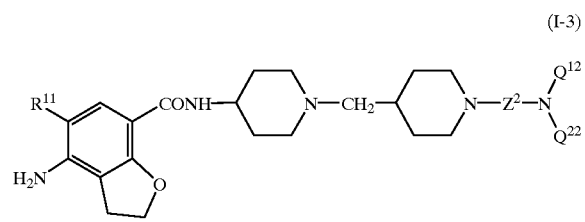

(I-3)

wherein $R^{11}$ is a chlorine atom or a bromine atom, $Z^2$ is —CO— or —CS—, $Q^{12}$ is a hydrogen atom, a methyl group, or an ethyl group, $Q^{22}$ is a methyl group, an ethyl group, or a phenyl group, or $Q^{12}$ and $Q^{22}$ may combine together with the nitrogen atom to which they bond to form a pyrrolidine ring, or a pharmaceutically acceptable acid addition salt thereof.

7. A compound of the formula (I-4):

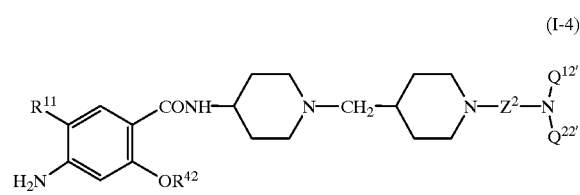

(I-4)

wherein $R^{11}$ is a chlorine atom or a bromine atom, $R^{42}$ is a methyl group, an ethyl group, or an isopropyl group, $Z^2$ is —CO— or —CS—, $Q^{12'}$ is a hydrogen atom, a methyl group, or an ethyl group, $Q^{22'}$ is a methyl group, an ethyl group, or a phenyl group, or $Q^{12'}$ and $Q^{22'}$ may combine together with the nitrogen atom to which they bond to form a pyrrolidine ring, or a pharmaceutically acceptable acid addition salt thereof.

8. A compound that is selected from the following compounds:

4-amino-5-chloro-N-[1-(1-dimethylcarbamoyl-4-piperidinylmethyl)-4-piperidinyl]-2,3-dihydrobenzo[b]furan-7-carboxamide;

4-amino-5-chloro-N-[1-(1-diethylcarbamoyl-4-piperidinylmethyl)-4-piperidinyl]-2,3-dihydrobenzo[b]furan-7-carboxamide;

4-amino-5-chloro-N-[1-(1-dimethylthiocarbamoyl-4-piperidinylmethyl)-4-piperidinyl]-2,3-dihydrobenzo[b]furan-7-carboxamide;

4-amino-5-chloro-N-[1-[1-(1-pyrrolidinecarbonyl)-4-piperidinylmethyl)-4-piperidinyl]-2,3-dihydrobenzo[b]furan-7-carboxamide; and 4-amino-5-chloro-N-[1-(1-phenylcarbamoyl-4-piperidinylmethyl)-4-piperidinyl]-2,3-dihydrobenzo[b]furan-7-carboxamide, or a pharmaceutically acceptable acid addition salt thereof.

9. A compound that is selected from the following compounds:

4-amino-5-chloro-N-[1-(1-dimethylcarbamoyl-4-piperidinylmethyl)-4-piperidinyl]-2-methoxybenzamide;

4-amino-5-chloro-N-[1-[1-(N-ethyl-N-methylcarbamoyl)-4-piperidinylmethyl]-4-piperidinyl]-2-methoxybenzamide;

4-amino-5-chloro-2-methoxy-N-[1-[1-(N-methyl-N-phenylcarbamoyl)-4-piperidinylmethyl]-4-piperidinyl]benzamide;

4-amino-5-chloro-N-[1-(1-dimethylthiocarbamoyl-4-piperidinylmethyl)-4-piperidinyl]-2-methoxybenzamide;

4-amino-5-chloro-2-methoxy-N-[1-[1-(1-pyrrolidinecarbonyl)-4-piperidinylmethyl]-4-piperidinyl]benzamide;

4-amino-5-chloro-N-[1-(1-dimethylcarbamoyl-4-piperidinylmethyl)-4-piperidinyl]-2-ethoxybenzamide;

4-amino-5-bromo-N-[1-(1-dimethylcarbamoyl-4-piperidinylmethyl)-4-piperidinyl]-2-methoxybenzamide;

4-amino-5-chloro- N-[1-(1-diethylcarbamoyl-4-piperidinylmethyl)-4-piperidinyl]-2-ethoxybenzamide;

4-amino-5-chloro-N-[1-(1-dimethylcarbamoyl-4-piperidinylmethyl)-4-piperidinyl]-2-isopropoxybenzamide;

4-amino-5-bromo-2-methoxy-N-[1-[1-(1-pyrrolidinecarbonyl)-4-piperidinylmethyl]-4-piperidinyl]benzamide;

4-amino-5-chloro-2- methoxy-N-[1-(1-phenylcarbamoyl-4-piperidinylmethyl)-4-piperidinyl]benzamide, and 4-amino-5-chloro-2-methoxy-N-[1-[1-(2-butanon-3-yl)-4-piperidinylmethyl]-4-piperidinyl]benzamide, or a pharmaceutically acceptable acid addition salt thereof.

10. A pharmaceutical composition, which contains as an active ingredient the compound as set forth in claim 1, or a pharmaceutically acceptable acid addition salt thereof.

11. A process for preparing a compound of the formula (I):

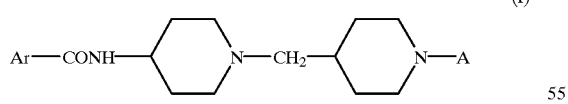
(I)

wherein Ar is a group of the following formula (Ar-1) or (Ar-2):

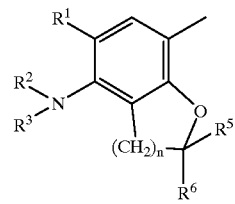
(Ar-1)

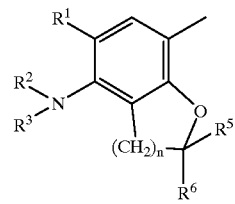
(Ar-2)

(in which $R^1$ is a halogen atom,
$R^2$ is a hydrogen atom or a lower alkyl group,
$R^3$ is a hydrogen atom, a lower alkyl group, or a lower alkanoyl group,
$R^4$ is a hydrogen atom or a lower alkyl group,
$R^5$ and $R^6$ are the same or different and each a hydrogen atom or a lower alkyl group, and
n is 1, 2 or 3),
A is a group of the following formula (A-1), (A-2) or (A-3):

(A-1)

(in which Z is —CO—, —CS— or —SO$_2$—,
$Q^1$ and $Q^2$ are the same or different and each a hydrogen atom, a lower alkyl group, a cycloalkyl group, a substituted or unsubstituted phenyl group, or a substituted or unsubstituted phenyl-lower alkyl group, or $Q^1$ and $Q^2$ may combine together with the nitrogen atom to which they bond to form a pyrrolidine ring, a piperidine ring, a hexahydroazepine ring, a morpholine ring, a thiomorpholine ring, or a piperazine ring having optionally a lower alkyl or benzyl substituent on the other nitrogen atom);

(A-2)

(in which $R^7$ is a hydrogen atom, a lower alkyl group, a lower alkoxy group, a lower alkoxycarbonyl group, a lower alkyl group being substituted by a hydroxy, lower alkoxy or lower alkoxycarbonyl group, or a substituted or unsubstituted phenyl group);

(A-3)

(in which p is 0, 1, 2, 3, 4 or 5,
$R^8$ is a hydrogen atom or a lower alkyl group, and
$R^9$ is a lower alkyl group or a lower alkoxy group), or a pharmaceutically acceptable acid addition salt thereof, which comprises the following process (a), (b), (c), (d), (e), or (f):

(a) when the compound (I) is a compound of the formula (I) wherein A is a group of the formula (A-1), reacting a compound of the formula (II):

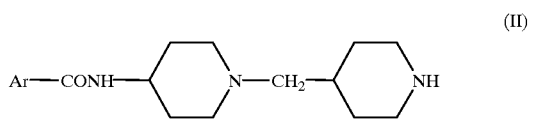
(II)

wherein Ar is the same as defined above, with a compound of the formula (III):

(III)

wherein X is a halogen atom, and Z, $Q^1$ and $Q^2$ are the same as defined above;

(b) when the compound (I) is a compound of the formula (I) wherein A is a group of the formula (A-1), $Q^1$ is a hydrogen atom, and Z is —CO— or —CS—, reacting a compound of the formula (II):

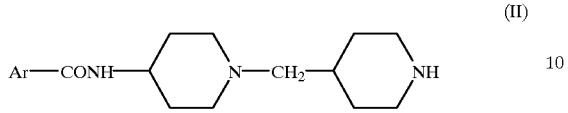

(II)

wherein Ar is the same as defined above, with a compound of the formula (IVa) or (IVb):

 (IVa)

 (IVb)

wherein $Q^{23}$ is the same substituents as those defined for the above $Q^2$, or a trimethylsilyl group;

(c) when the compound (I) is a compound of the formula (I) wherein A is a group of the formula (A-1), and Z is —CO—, reacting a compound of the formula (V):

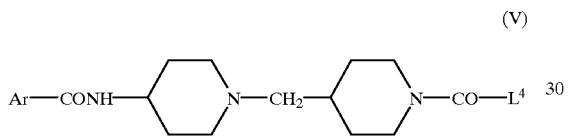

(V)

wherein $L^4$ is a leaving group, and Ar is the same as defined above, with a compound of the formula (VI):

 (VI)

wherein $Q^1$ and $Q^2$ are the same as defined above;

(d) reacting a compound of the formula (VII):

Ar—COOH (VII)

wherein Ar is the same as defined above, or a reactive derivative thereof, with a compound of the formula (VIII):

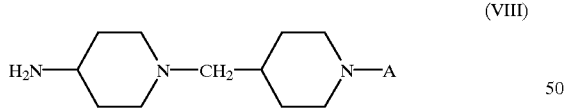

(VIII)

wherein A is the same as defined above;

(e) when the compound (I) is a compound of the formula (I) wherein A is a group of the formula (A-2), reacting a compound of the formula (II):

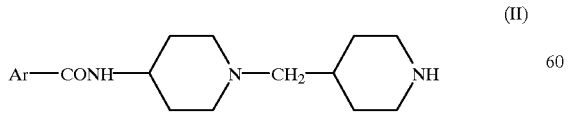

(II)

wherein Ar is the same as defined above, with a compound of the formula (A-2'):

 (A-2')

wherein $R^{72}$ is the same as $R^7$, or a reactive derivative thereof, provided that when (1) $R^{72}$ is a lower alkyl group being substituted by a hydroxy group, then a reactive derivative of the compound (A-2') should not be used, and when (2) $R^{72}$ is a lower alkoxy group, then an acid halide of the compound (A-2') is used; or (f) when the compound (I) is a compound of the formula (I) wherein A is a group of the formula (A-3), reacting a compound of the formula (II):

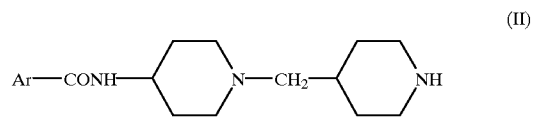

(II)

wherein Ar is the same as defined above, with a compound of the formula (A-3') or (A-3"):

 (A-3')

 (A-3")

wherein M is an alcoholic reactive ester residue, p' is 1, 2, 3 or 4, and $R^8$, $R^9$ and p are the same as defined above, and if necessary, followed by converting the product into a pharmaceutically acceptable acid addition salt thereof.

12. A serotonin 4 receptor agonist, which contains as an active ingredient the compound as set forth in claim 1, or a pharmaceutically acceptable acid addition salt thereof.

13. A method for treatment of diseases mediated by serotonin 4 receptors in patients, which comprises administering an effective amount of the compound as set forth in claim 1, or a pharmaceutically acceptable acid addition salt thereof, to a patient suffering from said diseases.

14. A pharmaceutical composition for the treatment of gastrointestinal motility disorders or gastrointestinal dysfunction, which contains as an active ingredient the compound as set forth in claim 1, or a pharmaceutically acceptable acid addition salt thereof in admixture with a pharmaceutically acceptable carrier or diluent.

15. A method for treatment of gastrointestinal motility disorders or gastrointestinal dysfunction, which comprises administering an effective amount of the compound as set forth in claim 1, or a pharmaceutically acceptable acid addition salt thereof, to a patient suffering from said diseases.

16. A compound of the formula (II-1):

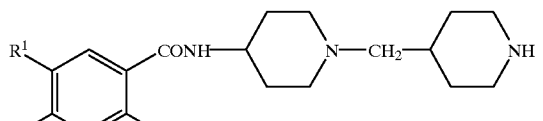

(II-1)

wherein $R^1$ is a halogen atom, $R^2$ is a hydrogen atom or a lower alkyl group, $R^3$ is a hydrogen atom, a lower alkyl group, or a lower alkanoyl group, and $R^4$ is a hydrogen atom or a lower alkyl group, or an acid addition salt thereof.

17. A compound of the formula (II-2):

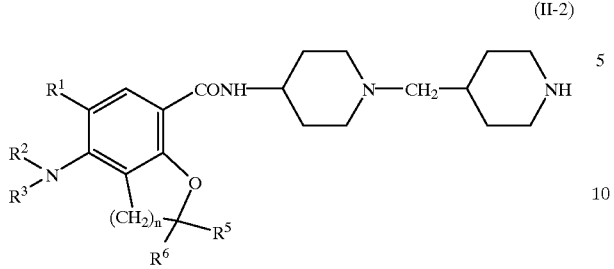

(II-2)

wherein $R^1$ is a halogen atom, $R^2$ is a hydrogen atom or a lower alkyl group, $R^3$ is a hydrogen atom, a lower alkyl group, or a lower alkanoyl group, $R^5$ and $R^6$ are the same or different and each a hydrogen atom or a lower alkyl group, and n is 1, 2 or 3,
or an acid addition salt thereof.

18. A compound of the formula (VIII):

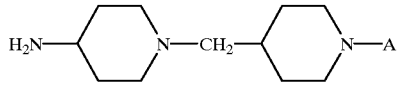

(VIII)

wherein A is a group of the following formula (A-1), (A-2) or (A-3):

—Z—N(Q$^1$)(Q$^2$)  (A-1)

(in which Z is —CO—, —CS— or —SO2—,
Q$^1$ and Q$^2$ are the same or different and each a hydrogen atom, a lower alkyl group, a cycloalkyl group, a substituted or unsubstituted phenyl group, or a substituted or unsubstituted phenyl-lower alkyl group, or Q$^1$ and Q$^2$ may combine together with the nitrogen atom to which they bond to form a pyrrolidine ring, a piperidine ring, a hexahydroazepine ring, a morpholine ring, a thiomorpholine ring, or a piperazine ring having optionally a lower alkyl or benzyl substituent on the other nitrogen atom);

—CO—R$^7$  (A-2)

(in which R$^7$ is a hydrogen atom, a lower alkyl group, a lower alkoxy group, a lower alkoxycarbonyl group, a lower alkyl group being substituted by a hydroxy, lower alkoxy or lower alkoxycarbonyl group, or a substituted or unsubstituted phenyl group);

—(CH$_2$)$_p$—CH(R$^8$)—COR$^9$  (A-3)

(in which p is 0, 1, 2, 3, 4 or 5,
R$^8$ is a hydrogen atom or a lower alkyl group, and
R$^9$ is a lower alkyl group or a lower alkoxy group), or a pharmaceutically acceptable acid addition salt thereof.

19. A method for treatment of a disease in a patient suffering from irritable bowel syndrome, flaccid constipation, habitual constipation, drug-induced constipation, chronic diarrhea, infant diarrhea, acute or chronic gastritis, reflux esophagitis, gastric neurosis, paralytic ileus after surgery, senile ileus, postgastrectomy syndrome, intestinal pseudo-obstruction, anorexia, nausea, vomiting, abdominal fullness, upper abdominal discomfort, visceral pain, heartburn, eructation, which comprises administering an effective amount of the compound as set forth in claim 1, or a pharmaceutically acceptable acid addition salt thereof, to the patient.

* * * * *